United States Patent
Mabon et al.

(10) Patent No.: US 11,292,756 B2
(45) Date of Patent: Apr. 5, 2022

(54) SURFACTANT PERFORMANCE THROUGH CARBON CHAIN EXTENSION AND LOWER BRANCHING

(71) Applicant: ExxonMobil Research and Engineering Company, Annandale, NJ (US)

(72) Inventors: Ross Mabon, Whitehall, PA (US); Shane Deighton, Bound Brook, NJ (US); Arben Jusufi, Belle Mead, NJ (US); Kanmi Mao, Basking Ridge, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/124,905

(22) Filed: Dec. 17, 2020

(65) Prior Publication Data

US 2021/0188749 A1 Jun. 24, 2021

Related U.S. Application Data

(60) Provisional application No. 62/950,424, filed on Dec. 19, 2019.

(51) Int. Cl.
| | |
|---|---|
| *C07C 31/125* | (2006.01) |
| *C07C 41/18* | (2006.01) |
| *C07C 43/13* | (2006.01) |
| *C07C 29/147* | (2006.01) |
| *C07C 67/08* | (2006.01) |

(52) U.S. Cl.
CPC .......... *C07C 31/125* (2013.01); *C07C 29/147* (2013.01); *C07C 41/18* (2013.01); *C07C 43/135* (2013.01); *C07C 67/08* (2013.01)

(58) Field of Classification Search
CPC ..... C07C 31/125; C07C 41/18; C07C 43/135; C07C 67/08
See application file for complete search history.

(56) References Cited

U.S. PATENT DOCUMENTS 5,644,041 A 7/1997 Johansson

FOREIGN PATENT DOCUMENTS

WO WO 2006024502 A2 * 3/2006 ............. C12P 41/00

OTHER PUBLICATIONS

Morr et al., English translation of WO 2006024502A2, Mar. 2006, pp. 1-8 (Year: 2006).*
Jackson E. Moore, "Wormlike micelle formation of novel alkyl-tri(ethylene glycol)-glucoside carbohydrate surfactants: Structure-function relationships and rheology", Journal of Colloid and Interface Science, 2018, vol. 529, pp. 464-475, Australia.

* cited by examiner

*Primary Examiner* — Rosalynd A Keys
(74) *Attorney, Agent, or Firm* — Robert A. Migliorini

(57) ABSTRACT

Provided herein are novel extended branched alcohols having a lower branching number and improved biodegradability when compared to other branched alcohols. Also provided are novel extended branched ethoxylates having surfactant properties which can be more efficient in reducing surface tension when compared to the ethoxylated form of other branched alcohols. Further provided are novel syntheses of making extended branched alcohols and extended branched ethoxylates.

14 Claims, 10 Drawing Sheets

SURFACTANT PERFORMANCE THROUGH CARBON CHAIN EXTENSION AND LOWER BRANCHING

FIELD OF THE INVENTION

The present invention relates to branched alcohols and more specifically relates to extended branched alcohols and ethoxylates thereof.

BACKGROUND OF THE INVENTION

EXXAL™ branched alcohols are used to make a wide range of regulatory compliant biodegradable non-ionic surfactants or ethoxylates (also referred to herein as "branched to ethoxylates"). The EXXAL™ branched alcohols help fulfill a demand for biodegradable surfactants that meet regulatory and voluntary standards without compromising on the quality of the formulation. More specifically, EXXAL™ branched alcohol ethoxylates provide the advantages of effectiveness, dynamic surface tension, rate of wetting, gel phase formation, foaming and low pour points.

For example, EXXAL™ branched ethoxylates are effective surfactants helpful in reaching lower minimum surface tension in water solutions. EXXAL™ branched ethoxylates can provide lower minimum surface tension values, but higher critical micelle concentrations than the linear equivalents. In addition, EXXAL™ branched ethoxylates often require less time to reach the desired surface tension than linear based ethoxylates.

Furthermore, EXXAL™ branched ethoxylates when used in industrial surfactants have been shown to have a reduced wetting time from 12 to 4 seconds: 3 times lower than comparable linear alcohol ethoxylates, resulting in lower processing times in applications like fast textile processing. The rate of wetting can impact process efficiencies, both in speed and evenness of application. Similarly, wetting performance leads to advantages in crop applications when active ingredients need to be quickly applied on surfaces.

Moreover, because gel phases can make product handling more difficult, gel phases are generally avoided in industrial applications. EXXAL™ branched ethoxylates can form fewer gel phases in water solutions than linear alcohols of comparable molecular weight. Due to this, solutions using EXXAL™-based ethoxylates remain fluid, providing a performance advantage for formulators or end users by improving product handling ability.

Despite these advantages, the surfactant industry faces the continued challenge of delivering biodegradable products that meet these performance requirements. As many in the industry maintain that there is a trade-off between biodegradability and performance, a need exists, therefore, for new branched alcohols and new branched ethoxylates that have increased biodegradability while maintaining the same advantages of the existing EXXAL™ branched alcohols and branched ethoxylates.

SUMMARY OF THE INVENTION

Provided herein are novel methods of synthesizing an extended branched alcohol comprising the steps of: (a) providing a branched alcohol; (b) reacting the branched alcohol with a half-ester to provide an extended branched ester; and (c) reducing the extended branched ester to provide an extended branched alcohol. In an aspect, the half-ester is monoethyl malonate. In an aspect, the extended branched ester is reduced by dissolving the extended branched ester in tetrahydrofuran. In an aspect, the extended branched alcohol has an average branching between about 0.5 and about 3.0.

Also provided herein are novel compounds of the formula:

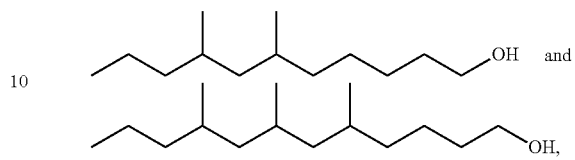

and mixtures of extended branched alcohols comprising one or more these compounds.

In addition, provided herein are novel compounds of the formula:

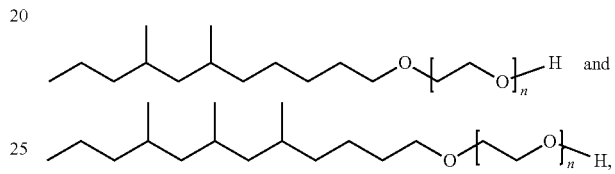

wherein n is an integer from 1 to 12, and mixtures comprising one or more of these compounds. Surfactants comprising one or more of these compounds are also described.

In an aspect, the present compounds are readily biodegradable in accordance with OECD 301 F. In an aspect, the compounds reduce surface tension between about 15 percent and about 20 percent when compared to the ethoxylated form of other branched alcohols.

Further provided are methods of making an extended branched alcohol comprising the steps of: (a) forming an aldehyde from a branched alcohol; (b) converting the aldehyde to form an extended branched ester; and (c) reducing the extended branched ester to produce an extended branched alcohol. In an aspect, an aldehyde is formed by hydrogen abstraction. In an aspect, the aldehyde is condensed with a reagent to form the extended branched ester.

Moreover, provided herein are methods of making extended branched ethoxylates comprising the steps of: (a) providing an extended branched alcohol; (b) converting the extended branched alcohol to a tosylate; and (c) converting the tosylate to an extended branched ethoxylate. Further provided are methods of making extended branched ethoxylates comprising the steps of: (a) removing hydrogen from a branched alcohol by hydrogen abstraction to form an aldehyde, wherein the branched alcohol undergoes in situ conversion into an alkene which is then hydrogenated to produce an extended branched ester; (b) reducing the extended branched ester to produce the extended branched alcohol; (c) converting the extended branched alcohol to a tosylate; and (d) converting the tosylate to an extended branched ethoxylate. In an aspect, the extended branched alcohol is converted to a tosylate by activation of an alcohol substituent of an extended branched alcohol by tosylation or substitution of halogenation. In an aspect, the tosylate is converted to an extended branched ethoxylate by reaction with an alkylene glycol or polyalkylene glycol.

DETAILED DESCRIPTION OF THE INVENTION

Figure 1A:
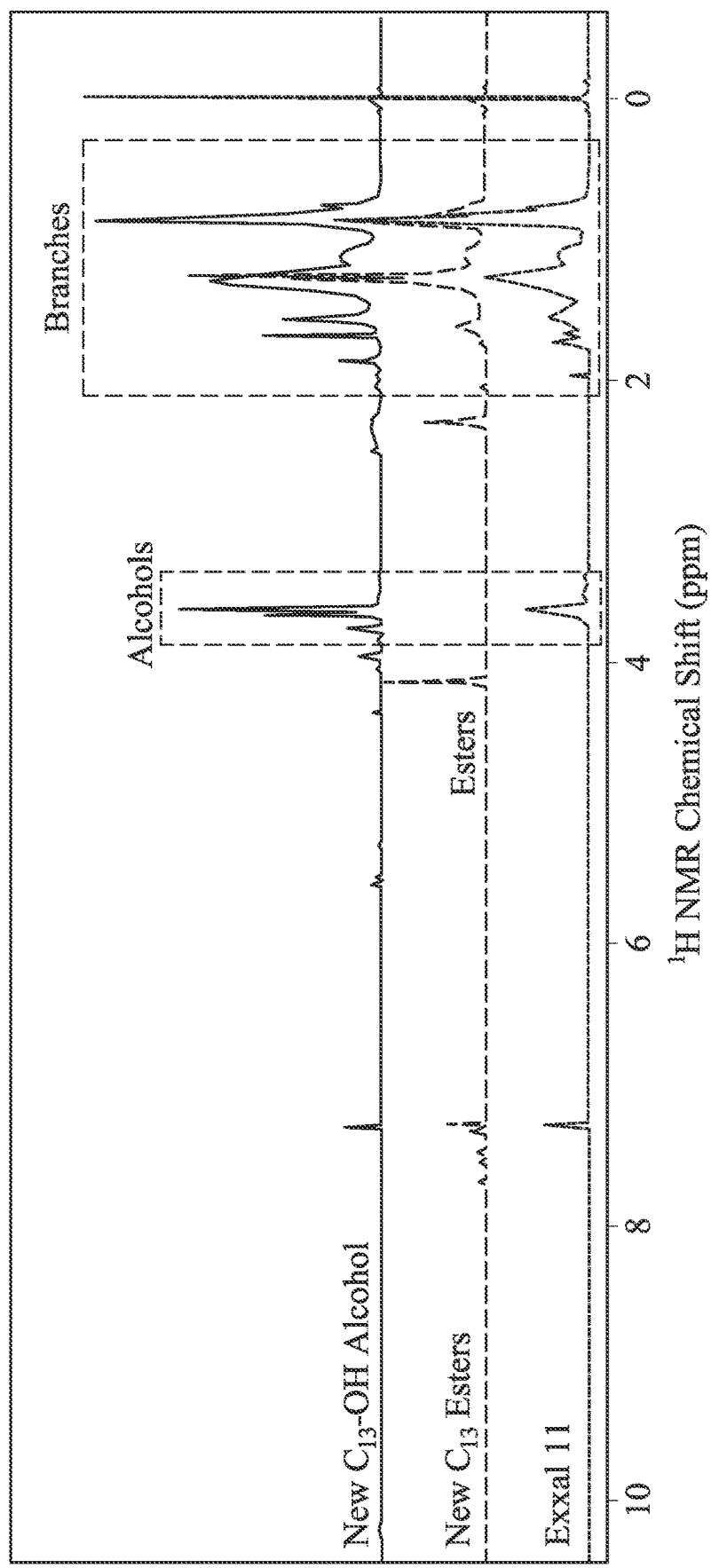
FIG. 1A is the $^1$H NMR spectra of EXXAL™ 11, the new $C_{13}$ extended branched esters (also referred to herein as "New $C_{13}$ esters"), and the new $C_{13}$ extended branched alcohols (also referred to as the "New $C_{13}$—OH alcohol").

Before the present compounds, components, compositions, and/or methods are disclosed and described, it is to be understood that unless otherwise indicated this disclosure is not limited to specific compounds, components, compositions, reactants, reaction conditions, ligands, catalyst structures, or the like, as such can vary, unless otherwise specified. It is also to be understood that the terminology used herein is for the purpose of describing particular embodiments only and is not intended to be limiting.

All numerical values within the detailed description and the claims herein are modified by "about" or "approximately" the indicated value, taking into account experimental error and variations.

For the sake of brevity, only certain ranges are explicitly disclosed herein. However, ranges from any lower limit can be combined with any upper limit to recite a range not explicitly recited, as well as, ranges from any lower limit can be combined with any other lower limit to recite a range not explicitly recited, in the same way, ranges from any upper limit can be combined with any other upper limit to recite a range not explicitly recited. Additionally, within a range includes every point or individual value between its end points even though not explicitly recited. Thus, every point or individual value can serve as its own lower or upper limit combined with any other point or individual value or any other lower or upper limit, to recite a range not explicitly recited.

For the purposes of this disclosure, the following definitions will apply:

As used herein, the terms "a" and "the" as used herein are understood to encompass the plural as well as the singular.

The term, "α carbon" refers to a carbon atom adjacent to a functional group in a functionalized hydrocarbon. In alcohols, the α carbon is the carbon atom adjacent to the alcohol group.

The term "biodegradability" refers to a substance's ability to be consumed aerobically by microorganisms. Biodegradability is expressed as a percent degradation during a specified time and is determined according to OECD 301 F. A substance is "readily biodegradable" if it reaches greater than 60% degradation in 28 days.

The term "cloud point" refers to the temperature at which a multi-phase solution containing a surfactant begins to cloud. Cloud point is measured according to ASTM D2024.

The term "critical micelle concentration" or "CMC" refers to the concentration of surfactant at which micelles form and all additional surfactant added to the system goes to micelles.

The term "dynamic surface tension" refers to a rate at which equilibrium surface tension is reached. Dynamic surface tension is expressed as the time required to reach equilibrium surface tension for a fixed surfactant concentration in water at 20° C. Dynamic surface tension is measured by maximum bubble pressure.

The term "esterification" refers to a reaction of a carboxylic acid moiety with an organic alcohol moiety to form an ester linkage. Esterification conditions can include, but are not limited to, temperatures of 0-300° C., and the presence or absence of homogeneous or heterogeneous esterification catalysts such as Lewis or Brønsted acid catalysts.

The term "hydroformylation" refers to an industrial process for the production of aldehydes from alkenes where the chemical reaction results in an addition of a formyl group (CHO) and a hydrogen atom to a carbon-carbon double bond. Hydroformylation is also known as an oxo synthesis or oxo process.

The term "hydrogenation" refers to a chemical reaction between molecular hydrogen ($H_2$) and a compound in the presence of a catalyst to reduce or saturate the compound.

The term "hydrophilic lipophilic balance" ("HLB") refers to a measure of the degree to which a surfactant is hydrophilic or lipophilic as determined on a 20-point scale. Higher HLB values indicate that the surfactant has increased hydrophilicity and water solubility. Conversely, lower values of HLB indicate the surfactant is hydrophobic and has lower water solubility. HLB can be determined by the Griffin method or the Davies method.

The term "Krafft point" refers to the minimum temperature to form micelles. Krafft point can be measured according to ASTM D2024.

The term "pour point" refers to the temperature below which the liquid loses its flow characteristics. Pour point is measured according to ASTM D5950.

The phrase "rate of wetting" refers to the time required to wet a standard cotton skein by a 1 g/L surfactant solution. Rate of wetting is measured according to the Draves test.

The present disclosure is directed to synthesis of new alcohols having a lower degree of branching than commercially available branched alcohols such as EXXAL™ branched alcohols. More specifically, new alcohols were achieved through chemical modification of commercial EXXAL™ 11 and EXXAL™ 13 branched alcohols, leading to extended branched alcohols such as the new $C_{13}$ extended branched alcohol ("New $C_{13}$—OH alcohol") and the new $C_{15}$ extended branched alcohol ("New $C_{15}$—OH alcohol")

described herein. Subsequently, ethoxylation of the extended branched alcohols produced novel surfactant molecules.

As described in the examples, in a first step, both commercial branched alcohols, EXXAL™ 11 and EXXAL™ 13 were chain extended by two carbons through a reaction with monoethyl malonate under basic conditions in the presence of a ruthenium catalyst to provide new $C_{13}$ extended branched esters ("New $C_{13}$ esters") and new $C_{15}$ extended branched esters ("New $C_{15}$ esters"). In a second step, the esters were converted to extended branched alcohols by reduction of the esters with lithium aluminum hydride ("LiAlH$_4$"). Nuclear magnetic resonance ("NMR") spectroscopy confirmed that the new $C_{13}$ extended branched alcohols ("New $C_{13}$—OH alcohol") and new $C_{15}$ extended branched alcohols ("New $C_{15}$—OH alcohol") have the same branching characteristics as the starting materials, commercially available EXXAL™ 11 branched alcohols and EXXAL™ 13 branched alcohols. In another step, the extended branched alcohols were converted to tosylates through reaction with p-toluenesulfonyl chloride ("TsCl"). The tosylates were then converted to new $C_{13}$ extended branched ethoxylates ("New $C_{13}$ ethoxylate") and new $C_{15}$ extended branched ethoxylates ("New $C_{15}$ ethoxylate") by reaction with octaethylene glycol in the presence of sodium hydride ("NaH").

The present extended branched alcohols have a lower branching number and can provide improved biodegradability when compared to other branched alcohols. The extended branched ethoxylates have surfactant properties and can be about 15% to about 20% more efficient in reducing surface tension when compared to the ethoxylated form of other branched alcohols. Moreover, the New $C_{15}$—OH alcohols provide an extension toward the high carbon number limit of the EXXAL™ alcohol family, that is, 15 carbons instead of currently 13.

Currently, commercial EXXAL™ 13-derived surfactants are sold in the industrial surfactant market, the largest surfactant market being the household detergent industry. The present extended branched alcohols and ethoxylates enable improved biodegradability rates and better efficiencies (up to 15 to 20% improvement). Further, this novel synthesis increases utilization of commercial EXXAL™ 11 branched alcohols, which can serve as supplemental supplies for the commercial EXXAL™ 13 branched alcohol products. Moreover, new $C_{15}$ extended branched alcohols extend the portfolio range and can be used in new surfactant applications, e.g. oil soluble detergents, drilling fluids.

Commercially Available EXXAL™ Branched Alcohols

Commercially available EXXAL™ branched alcohols are mixtures of long-chain, primary aliphatic branched alcohols, secondary aliphatic branched alcohols and isomers thereof. For example, EXXAL™ 11 includes $C_{10}$, $C_{11}$, and $C_{12}$ hydrocarbons, has about 87 wt % of $C_{11}$ hydrocarbons, and has an average branching number of about 2.20. Tables 1A and 1B immediately below provide carbon number distributions and average branching of several EXXAL™ branched alcohols.

TABLE 1A

| | Average Carbon Number Distribution by GC (wt %) | | | | | | | | | Average Branching #branches/molecule |
|---|---|---|---|---|---|---|---|---|---|---|
| | $C_6$ | $C_7$ | $C_8$ | $C_9$ | $C_{10}$ | $C_{11}$ | $C_{12}$ | $C_{13}$ | $C_{14}$ | |
| EXXAL™ 8 | <0.1 | 1.8 | 92.7 | 5.2 | 0.2 | | | | | 1.61 |
| EXXAL™ 9 | | | 3 | 77.1 | 18.8 | 1.1 | | | | 1.87 |
| EXXAL™ 10 | | | | 6.4 | 88.2 | 5.2 | | | | 2.06 |
| EXXAL™ 11 | | | | | 6.7 | 87 | 6.3 | | | 2.20 |
| EXXAL™ 13 | | | | 0.17 | 0.3 | 1.4 | 21.5 | 70.1 | 6.7 | 3.07 |

TABLE 1B

Spec Limits Max

| | | | |
|---|---|---|---|
| EXXAL™ 8 | $C_6 + C_{10}^+$ 2.0 | $C_7$ 3.5 | $C_9$ 2.0-9.0 |
| EXXAL™ 9 | $C_8$ 6.0 | $C_{10}$ 18-22 | $C_{11}^+$ 2.5 |
| EXXAL™ 10 | $C_8$ 0.75 | $C_9$ 10.0 | $C_{11}^+$ 7.0 |
| EXXAL™ 11 | $C_{10}^-$ 6.7 | $C_{11}$ 87.0 | $C_{12}^+$ 6.3 |
| EXXAL™ 13 | $C_9 + C_{10}$ 2.0 | $C_{14}^+$ 10.0 | |

In addition to the data presented above, other characteristics were determined for the EXXAL™ branched alcohols shown in Tables 1A and 1B. The percentage a branching is estimated to be between about 10% and about 15% for each of the EXXAL™ branched alcohol mixtures. The percentage of quaternary carbons is estimated to be between about 1% and about 2% for each of the EXXAL™ branched alcohols. Furthermore, EXXAL™ 13 can have an average carbon number between about 12.6 and about 12.7, an average number of branches per molecules between about 2.90 and about 3.07 and can comprise between about 60 wt % $C_{13}$ and about 70.1 wt % $C_{13}$. See U.S. Patent Appl. Nos. 2011/0313090 Table 1 and 2011/0184105 Table 1, incorporated herein by reference.

Objective criteria and recognized test methods show that EXXAL™ branched alcohols and ethoxylates readily biodegrade. The test methods include EPA- and EU-approved tests such as an OECD 301F manometric respirometry test that assesses "ultimate" biodegradation, or breakdown of the substance by microorganisms, resulting in the production of carbon dioxide, water, mineral salts and new biomass. The criterion to "pass" as readily biodegradable in OECD 301F test is to reach 60% degradation in 28 days (for constituent substances it is the same within a "10-day window"). EXXAL™ branched alcohols and the ethoxylates meet the OECD readily biodegradable threshold for isomeric mixtures. Specifically, both EXXAL™ 11 and EXXAL™ 13 are readily biodegradable: EXXAL™ 11 demonstrated 71% degradation in 28 days and EXXAL™ 13 demonstrated 61% degradation in 28 days, both measured according to OECD 301 F.

EXXAL™ branched alcohol mixtures contain isomers having different branching structures. As to linear chains, EXXAL™ branched alcohols' purity exceeds 99%. High-purity EXXAL™ branched alcohols exhibit reactivity typical of higher primary alcohols. Having a branched structure, EXXAL™ branched alcohols are characterized by low pour points. While linear $C_{12}$-$C_{14}$ alcohols have pour points around room temperature (20° C.), branched alcohols such as EXXAL™ 13 have pour points lower than −40° C. Lower pour points have the advantage of reducing the need for heated tanks and lines for operations in colder climates, which in turn can lower energy bills and reduce handling costs.

Table 2 immediately below provides additional physical properties of EXXAL™ branched alcohols.

of a catalyst to form aldehydes and alcohols containing one carbon atom more than the feed olefin. See e.g., U.S. Pat. No. 6,482,972. The primary hydroformylation reaction is a reaction of olefin with carbon monoxide and hydrogen to produce aldehydes:

Olefin+CO+$H_2$→Aldehyde.

There are a number of simultaneous competing and consecutive reactions including:

Olefin+$H_2$→Paraffin;

Aldehyde+$H_2$→Alcohol; and

Aldehyde+CO+$H_2$→Formate ester,

TABLE 2

|  | EXXAL™ 8 | EXXAL™ 9 | EXXAL™ 10 | EXXAL™ 11 | EXXAL™ 13 |
| --- | --- | --- | --- | --- | --- |
| Chemical Name | Isooctanol | Isononanol | Isodecanol | Isoundecanol | Isotridecanol |
| Acid Value Mg KOH/g ASTM D1045 | <0.05 | <0.05 | <0.05 | <0.10 | <0.03 |
| Boiling Range ° C. ASTM D1078 | 186-192 | 204-214 | 218-224 | 233-239 | 255-263 |
| Carbonyl Number Mg KOH/g ISO 1843-1 ASTM E411 | <0.20 | <0.20 | <0.20 | <0.20 | <0.20 |
| Color Pt/Co ASTM D5386 | 5 | 5 | 5 | 5 | 5 |
| Density 20° C. g/cm³ ASTM D4052 | 0.831 | 0.835 | 0.838 | 0.841 | 0.846 |
| Flash Pt. PMCC ° C. ASTM D93 | >70 | >80 | >90 | >100 | >100 |
| Hydroxyl Number Mg KOH/g ISO 1843-5 | 425 | 377 | 350 | 321 | 285 |
| Pour Pt. ° C. ASTM D5950 | <−40 | <−40 | <−40 | <−40 | <−40 |
| Viscosity at 20° C. Mm²/s ASTM D445 | 12 | 17 | 21 | 27 | 48 |
| Water content Wt % ISO 12937 | <0.1 | <0.1 | <0.1 | <0.1 | <0.1 |

Furthermore, EXXAL™ 13 can have a boiling range between about 253° C. and about 265° C., a hydroxyl number of about 285 mg KOH/g, a carbonyl number between about 0.1 mg KOH/g and about 0.2 mg KOH/g, a water content between about 0.05 wt % and about 0.1 wt % and a viscosity at 20° C. between about 17 mm²/s and about 48 mm²/s. See U.S. Patent Appl. No. 2011/0184105 Table 1a, incorporated herein by reference.

Methods of Making Branched Alcohols: High Pressure Oxo Process

To synthesize the present extended branched alcohols and extended branched ethoxylates, starting alcohols are available from Exxon Chemical Company under the trade name EXXAL. As described herein, EXXAL™ products are mixtures of branched primary alcohols having a mix of carbon numbers and isomers which are produced by catalytic hydroformylation or carbonylation of higher olefin feedstocks.

Hydroformylation is a process in which an olefin is reacted with carbon monoxide and hydrogen in the presence where the aldehydes can condense with alcohols to form a hemi-acetal, $R^1$—CHOH—O—$R^2$, that is not very stable and can form an unsaturated ether to further react as follows:

Unsaturated ether+$H_2$→di-alkyl ether; and

Unsaturated ether+CO+$H_2$→ether aldehyde, where $R^1$ and $R^2$ independently represent alkyl chains and can be the same or different, unbranched (linear) or branched. Aldehydes can further condense with two alcohols to form an acetal, $R^1$—(O—$R^2$)$_2$.

Commercial hydroformylation processes are either a low or medium pressure process, or a high or medium pressure process. The low or medium pressure process typically involves the use as catalyst of an organometallic complex of rhodium with organophosphate ligands for providing the necessary stability at the lower pressures, and operates at pressures from 10 to 50 bar. The high or medium pressure process operates at pressures from 50 to 350 bar. Generally, low pressure processes are used for hydroformylation of unbranched and terminal, primarily lower olefins such as ethylene, propylene and n-butene, but can include n-hexene-1, n-octene-1 and mixtures of higher carbon number terminal olefins produced by the Fischer-Tropsch process. On the other hand, the high-pressure hydroformylation process is used for linear and branched higher olefins such as those containing 5 or more carbon atoms to produce higher alcohols, aldehydes or acids in the $C_6$ to $C_{15}$ range, particularly the $C_9$ to $C_{13}$ range. High-pressure hydroformylation processes ("oxo reactions") involve the reaction of liquid materials with gaseous materials at least partially dissolved in the liquid during reaction. Gaseous materials can be entrained as droplets or bubbles in the liquid phase.

Starting materials of the high-pressure hydroformylation process include olefins or mixtures of olefins such as those obtained from olefin oligomerization units. For example, the olefins can be mixtures of $C_{15}$ to $C_{12}$ olefins obtained by the phosphoric acid-catalyzed oligomerization of $C_3$ and $C_4$ olefins and mixtures thereof. The olefin mixtures can be fractionated to obtain relatively narrow boiling cut mixtures of particular carbon number, which in turn can produce aldehydes and alcohols with the desired carbon number.

Alternatively, the olefins can be obtained by other oligomerization techniques such as dimerization or trimerization of butene using a nickel or nickel oxide catalyst, like the OCTOL® process or the process described in U.S. Pat. No. 6,437,170, or an oligomerization process for ethylene, propylene and/or butenes using a nickel salt and involving di-alkyl aluminum halides, like the range of DIMERSOL® processes, or a zeolite or a molecular sieve catalyst.

Olefins can also be obtained from ethylene processes, in which case $C_6$, $C_8$, $C_{10}$, or $C_{12}$, or even higher carbon numbers such as up to $C_{14}$, $C_{16}$, $C_{18}$, or even $C_{20}$ can be produced. Olefins can be mixtures obtained from the Fischer Tropsch process, which primarily contain terminal olefins but can have side branches along the longest alkyl chain, and which can also contain some internal olefins, linear and branched. The starting materials for the oligomerization units can be obtained from fluid catalytic cracking, steam cracking of gasses such as ethane and propane, liquids such as liquefied petroleum gas of naphtha, gasoil or heavier distillate, or whole crude from oxygenate-to-olefin processes and/or paraffin dehydrogenation processes.

The gaseous materials involved in the high pressure oxo process include carbon monoxide and hydrogen, frequently supplied in a mixture that is known as synthesis gas or "syngas". Syngas can be obtained through the use of partial oxidation technology, or steam reforming, or a combination thereof that is often referred to as autothermal reforming. It can be generated from almost every carbon-containing source material, including methane, natural gas, ethane, petroleum condensates like propane and/or butane, naphtha or other light boiling hydrocarbon liquids, gasoline or distillate-like petroleum liquids, and heavier oils and byproducts from various processes including hydroformylation, and even from coal and other solid materials like biomass and waste plastics. When using liquid feeds, a steam reformer can involve a pre-reformer to convert part of the feed to methane before entering the actual reformer reaction.

In an industrial hydroformylation plant producing alcohols, at least part of a hydroformylation product includes mixtures of alcohols, aldehydes and formate esters, and various other compounds, which can be subsequently hydrogenated to convert the aldehydes and formate esters to alcohols and reduce the level of the impurities. By way of example, conditions for hydrogenation are described in WO 2005/058782 at 3, 1. 8 to 9, 1. 10 and 25, 1. 18 to 36, 1. 20, incorporated herein by reference.

Hydroformylation reactions can be continuous or batch reactions. The continuous reactions generally take place in a series of two or more reactors. In an aspect, reactions can take place in a series of reactors involving gas lift reactors as lead or front-end reactors. In an aspect, the series of reactors can be loop reactors. The series of reactors can be separate distinct sections within one, or more than one, reaction vessel. Alternatively, one reactor in the series can comprise different volumes in series or in parallel.

The high pressure oxo process has three stages. In a first stage, or oxonation reaction, olefinic material and proper proportions of CO and $H_2$ are reacted in the presence of a carbonylation catalyst to yield a product comprising aldehydes having one more carbon atom than olefin reacted. Typically, alcohols, paraffins, acetals, and other species are also produced. An oxygenated organic mixture can contain various salts and molecular complexes of metal from catalyst (a "metal value") and is sometimes referred to as a crude aldehyde, or a crude hydroformylation mixture. In a second stage, or de-metaling stage, metal values are separated from crude aldehyde, such as by injecting dilute acetic acid. The crude hydroformylation mixture is then separated into phases: an organic phase comprising aldehyde separated from an aqueous phase. The organic phase is then converted to final product using downstream unit operations. In a third stage of the high pressure oxo process, metal values are processed for use in another process. These process stages can occur in three distinct vessels with numerous variations and improvements. Alternately, the stages can be combined.

Suitable processes to produce branched alcohols having from 6 to 15 carbon atoms per molecule are disclosed in numerous publications, for example in WO 2005/058782, WO 2005/58787, WO 2008/128852, WO 2008/122526, WO 2006/086067, WO 2010/022880, and WO 2010/022881. Certain processes can employ a "Kuhlmann" cobalt catalyst cycle, such as the process disclosed in WO 2008/122526. Improvements in efficiency of raw materials used, optimization of the recycle of unreacted materials, and the optimization of reaction conditions, material balance and other variables, can result in increases in conversion, output and efficiency. For example, oxonation processes occur in a reactor having an operating pressure between about 300 psig and about 1500 psig, an operating temperature between about 125° C. and about 200° C., a catalyst to olefin ratio of between about 1:1 and about 1:1000, and a molar ratio of hydrogen to carbon monoxide between about 1:1 and about 10:1. See, WO 03/082788 A1 at ¶ [0039].

Methods of Making Extended Branched Alcohols

The present extended branched alcohols are novel surfactant precursors that can be produced from the commercial EXXAL™ branched alcohols by different methods and processes. Alcohols are generally poor electrophiles for alkylation reactions, requiring activation of the hydroxyl into a suitable leaving group in order to facilitate nucleophilic substitution. Therefore, one strategy for alcohol activation involves the removal of hydrogen from the alcohol to form an aldehyde, which undergoes in situ conversion into an alkene prior to return of hydrogen to afford a net alkylation process. This oxidation/alkene-formation/reduction sequence has been referred to as a "borrowing hydrogen" methodology. See, Pridmore, Simon J., et al., *C—C Bond Formation from Alcohols and Malonate Half Esters Using Borrowing Hydrogen Methodology*. Tetrahedron Letters, 49 (2008) 7413-7415.

More specifically, in the borrowing hydrogen methodology, alkylation reactions of alcohols can be achieved using simple esters and the conversion of ROH into $RCH_2CO_2R'$ and malonate half-esters as convenient reagents for alkylation reactions according to the pathway outlined in a general Scheme I below. Id.

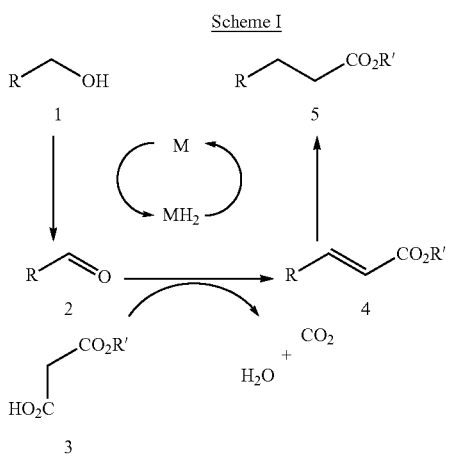

Scheme I

Using Scheme I, temporary removal of hydrogen from alcohol 1 generates an aldehyde 2 which undergoes a decarboxylative Knoevenagel reaction with malonate half ester 3, yielding the α, β-unsaturated ester 4. Return of the hydrogen by alkene reduction would then provide the overall alkylation product 5. The decarboxylative Knoevenagel reaction of aldehydes is a process, which is usually catalyzed by a suitable amine. Id. citing Klein, J, et al., J. Am. Chem. Soc. 1957, 79, 3452. The only by-products formed in the decarboxylative Knoevenagel reaction are water and carbon dioxide. Hence, the process provides a useful reaction for the conversion of aldehydes into α, β-unsaturated esters.

An exemplary reaction is shown in Scheme II immediately below:

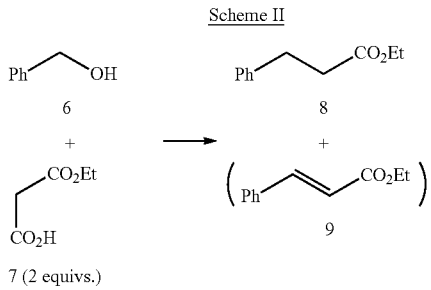

Scheme II

In this process, a benzyl alcohol 6 reacts with monoethyl malonate 7 to convert the benzyl alcohol 6 into ethyl dihydrocinnamate 8 (an alkylated product) and alkene byproduct 9.

For borrowing hydrogen methodologies, various catalysts can be used including Ru or Ir catalysts. Further, pyrrolidine can be used as an organo-catalyst based on its ability to affect the decarboxylative Knoevenagel reaction. Id. citing Klein, J., et al., J. Am. Chem. So. 1957 79, 3452. For example, the following transition metals can convert alcohol into alkylated product: (i) $Ru(PPh_3)_3$-$(CO)H_2$/xantphos which is also useful in hydrogen transfer reactions; (ii) $Ru(PPh_3)_3C_{12}$/KOH as a readily available Ru(II) source; and (iii) $[Cp*IrCl_2]_2/Cs_2CO_3$ for a good effect in C—C and C—N bond-forming reactions from alcohols. Id. citing Fujita, K., Synlett 2005, 560.

A summary of exemplary reactions for formation of ester 5 from alcohol 1 are provided in Table 3 below:

TABLE 3

| Catalyst[a] | Conv.[b] (%) | Time (h) | 8:9 C—C:C═C |
|---|---|---|---|
| $Ru(PPH_3)_3(CO)H_2$/xantphos | 100 | 24 | 62:38 |
| $Ru(PPH_3)_3Cl_2$/KOH | 100 | 24 | 92:8 |
| $Ru(PPH_3)_3Cl_2$/KOH | 93 | 4 | 82:11 |
| $[Cp*IrCl_2]_2/Cs_2CO_3$ | 100 | 24 | 100:0 |
| $[Cp*IrCl_2]_2/Cs_2CO_3$ | 79 | 4 | 76:3 |

[a]Catalyst loading was 2.5 mol % (i.e., 2.5 mol % in Ru or 5 mol % Ir).
[b]Conversion was established by analysis of the $^1$H NMR spectrum.

Pridmore, Simon J., et al., *C—C Bond Formation from Alcohols and Malonate Half Esters Using Borrowing Hydrogen Methodology*. Tetrahedron Letters, 49 (2008) 7413-7415 at 7414.

As set out in Table 3, a comparison of conversions achieved after four hours using the $Ru(PPh_3)_3C_{12}$/KOH and $[Cp*IrCl_2]_2/Cs_2CO_3$ catalysts revealed that the ruthenium catalyst was slightly more effective. As reported, effective catalyst loading can be lower for a Ru catalyst than an Ir catalyst. Further, in order to overcome any problems of unreacted alkene, isopropanol can act as a hydrogen donor to replace any lost $H_2$.

More generally, alcohols can be converted into the doubly homologated esters 10 using Scheme III below.

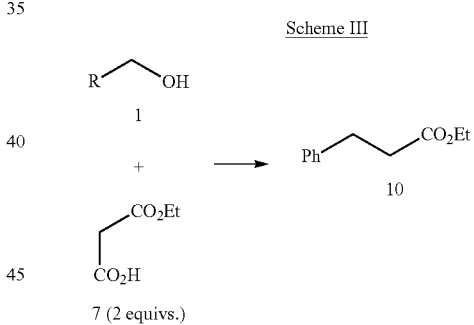

Scheme III

In an aspect, alcohol 1 and malonate half ester 7 are combined with 2.5 mole % $Ru(PPh_3)_3C_{12}$, 6.25 mole % KOH, 30 mole % pyrrolidine and 20 mole % $(CH_3)_2CHOH$ and refluxed for 24 hours. Noteworthily, electron-deficient alcohols and aliphatic alcohols can be less reactive and can require a higher catalyst loading to reach completion. The lower reactivity of the alcohol parallels the expected ease of oxidation for the substrate.

By using borrowing hydrogen methodology and malonate half esters, EXXAL™ branched alcohols can be converted into doubly homologated esters (also referred to herein as extended branch esters) which can undergo a decarboxylative Knoevenagel reaction on the intermediate aldehyde to produce the present new $C_{13}$ extended branched alcohols and new $C_{15}$ extended branched alcohols.

Alternative methods for producing the present extended branched alcohols include α-alkylation of esters. In these processes, α-alkylation of esters utilizes the alcohol as an alkylating agent. Industrially, alcohols are typically more environmentally benign and less expensive than alkyl halides. Hence, alkylation with primary alcohol(s) using the "borrowing hydrogen" methodology have emerged as green processes for C—C bond formations. See, Guo, L. et al., *A General and mild Catalytic Alkylation of Unactivated Esters Using Alcohols*, Angew. Chem. Int. Ed. 2015, 54, 4023-4027.

By way of example as shown in Scheme IV below, the primary alcohol is varied using an NCP/Ir catalyst and operating under optional reaction conditions, benzylic alcohols 11 (containing both electron-donating and electron-withdrawing groups) alkylated efficiently. Id. at 4024.

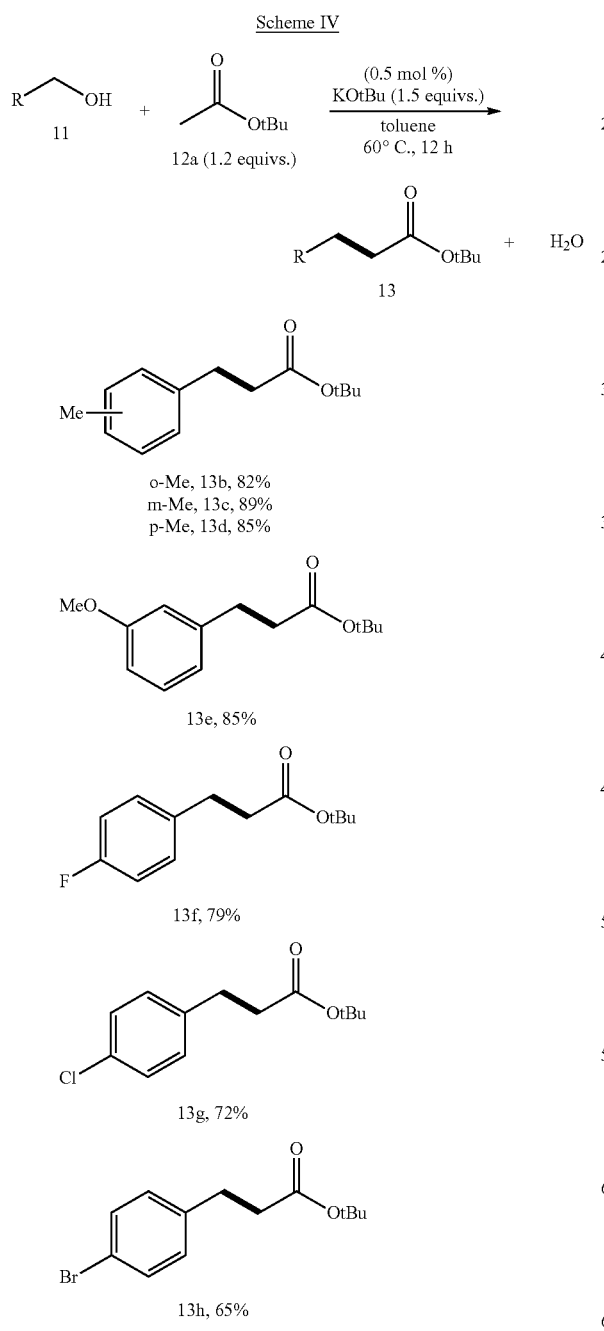

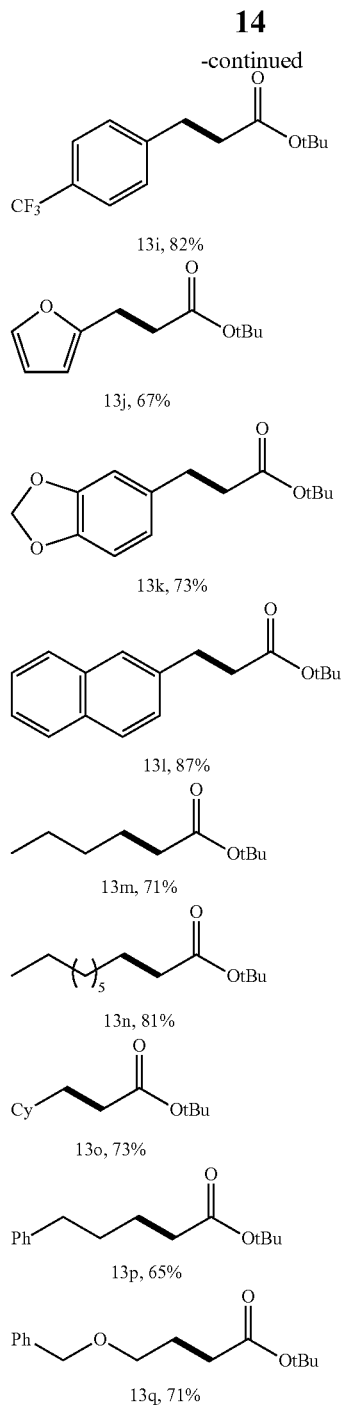

As reported, couplings of nonbenzylic primary alcohols (11m-q) and 12a formed products 13m-q in useful yields. Id. The catalyst system allowed for the alkylation of un-activated substituted esters with primary alcohols. Id.

Suitable catalysts for ester alkylation with alcohol can include, but are not limited to, pincer-type iridium catalysts used at low catalyst loading with alcohol to ester ratios of about 1:1. Pincer-type iridium catalysts can include NCP, PCP, POCOP complexes, and the like.

Extended branched esters can be then converted to extended branched alcohols by reduction. By way of example, reduction of an extended branched ester 14 using lithium aluminum hydride to yield the corresponding extended branched alcohol 15 is shown below in Scheme V.

Here the alkyl ester is reduced to an alcohol to provide the present extended branched alcohols.

Scheme V

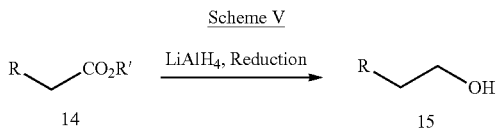

Other alternative methods of producing extended branched alcohols can include reduction of an unsaturated extended branched ester 16 to extended branched alcohol 17 using catalytic hydrogenation as shown in Scheme VI immediately below. Similar reduction chemistries capable of reducing esters and double bonded carbons can also be used. Reduction of an unsaturated extended branched ester 16 to the extended branched alcohol 17 can be performed stepwise through saturation of the double bond first, followed by the reduction of the ester. Similarly, the ester of the unsaturated extended branched ester 16 can be reduced or hydrolyzed first, followed by reduction to the extended branched alcohol 17.

Scheme VI

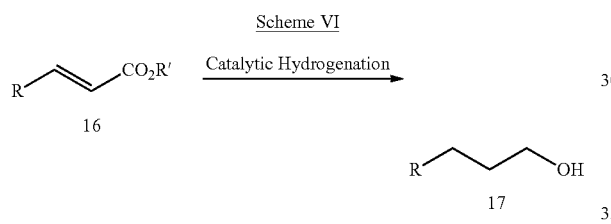

Another alternative for the production of the extended branched alcohols provided herein includes a process of oxidation of an alcohol to an aldehyde, followed by olefination and reduction to yield the extended branched alcohols. As shown in Scheme VII below, methods of olefination are preceded by the oxidation of an alcohol using the (a) Parikh-Doering protocol to generate the corresponding aldehyde, followed by a (b) Horner-Wadsworth-Emmons olefination to give unsaturated ester 19. Such processes include stepwise oxidation and olefination and are described by Dineen T A, et al., *Total Synthesis of Cochleamycin A*, Org Lett. Vol 6, (2004) 2043-2046.

Scheme VII

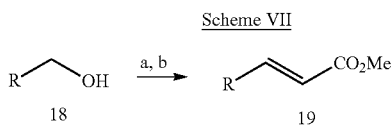

Similarly, two-carbon extension of alcohol by oxidation, olefination, and then reduction is shown below in Scheme VIII. Oxidation of primary alcohol 24 by using the Parikh-Doering protocol gave the corresponding aldehyde, which was subjected to standard Horner-Wadsworth-Emmons olefination to give ester 25. Reduction of 25 with DIBAL-H gave allylic alcohol 26. A subsequent hydrogenation of allylic alcohol 26 would then yield an extended branched alcohol.

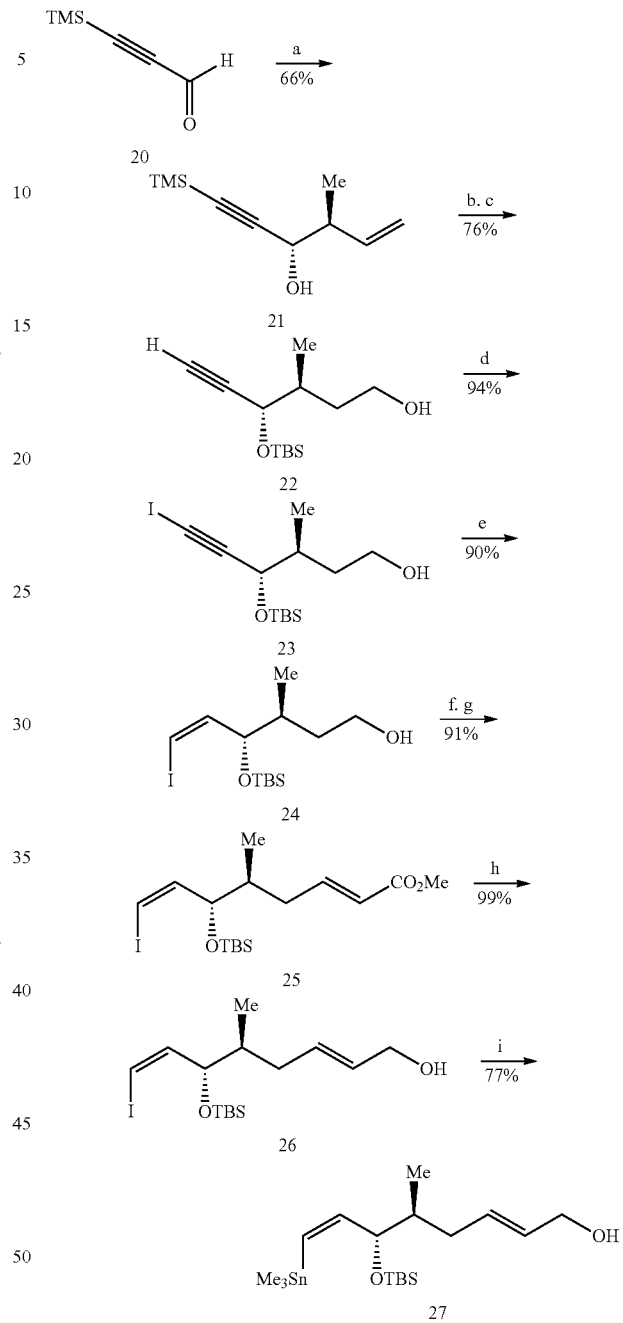

Conditions for Scheme VIII have been reported as: (a) ($^d$Ipc)$_2$B-crotyl, THF, −78° C., then NaBO$_3$.H$_2$O. (b) TBS-OTf, 2,6-lutidine, CH$_2$Cl$_2$, −78° C. (c) 9-BBN, THF, then aqueous NaOH/H$_2$O$_2$. (d) n-BuLi, THF, −50° C., then I$_2$. (e) o-Nitrobenzenesulfonylhydrazide, Et$_3$N, THF/i-PrOH (1:1). (f) SO$_3$.pyr, DMSO, iPr$_2$NEt, CH$_2$Cl$_2$, 0° C. (g) Trimethyl phosphonoacetate, LiCl, Et$_3$N, CH$_3$CN. (h) DIBAL-H, CH$_2$Cl$_2$. (i) MeLi, Et$_2$O, −40 to 23° C.; n-BuLi, −78° C.; then Me$_3$SnCl, THF, −78° C. Id. at 2044.

Construction of fragment 27 began with asymmetric (E)-crotylboration of aldehyde 20, which gave anti homoallylic alcohol 21. Protection of the hydroxyl group of 21 as a TBS ether and then hydroboration of the vinyl group with 9-BBN and cleavage of the alkynylsilane unit during oxidation of the alkylborane provided primary alcohol 22. This intermediate was iodinated in 94% yield by treatment with n-BuLi in THF (−50° C.) and then $I_2$. (Z)-Vinyl iodide 24 was then prepared in by reduction of alkynyl iodide 23 with a diimide (generated in situ from o-nitrobenzenesulfonylhydrazide and $Et_3N$). Oxidation of primary alcohol 24 by using the Parikh-Doering protocol gave the corresponding aldehyde, which was subjected to standard Homer-Wadsworth-Emmons olefination to give ester 25. Reduction of 25 with DIBAL-H gave allylic alcohol 26. Finally, sequential treatment of 26 with MeLi ($Et_2O$, −78° C.) and then n-BuLi (−78° C.), followed by addition of $Me_3SnCl$, then provided vinylstannane 27. Id.

Generally, Scheme VIII describes a process of oxidizing primary alcohol 24 using the Parikh-Doering protocol, subjecting the resulting aldehyde to Horner-Wadsworth-Emmons olefination to yield ester 25, and reduction to yield allylic alcohol 26. A further step of hydrogenating allylic alcohol 26 could be taken to produce a primary alcohol. Hence, this process can be utilized to produce the present extended branched alcohols.

The present extended branched alcohols can be used as chemical intermediates in the manufacture of plasticizers, detergents, solvents and the like, or in the production of lubricant esters such as the esters of phthalic acid and anhydride, esters of cyclohexane mono- or dicarboxylic acids, esters of adipic or tri-mellitic acid, esters of the various isomers of pyromellitic acid and polyol esters. More specifically, the extended branched alcohols can be used in surfactant derivatives as described below.

Methods of Making Extended Branched Ethoxylates

Alcohol ethoxylates are a class of compounds that are used throughout many industrial practices and commercial markets. Generally, these compounds are synthesized via the reaction of a branched alcohol and ethylene oxide, resulting in a molecule that consists of two main components: (1) an oleophilic, carbon-rich, branched alcohol also referred to herein as a hydrophobic moiety; and (2) a hydrophilic, polyoxyethylene chain also referred to herein as a hydrophilic moiety.

Due to the basic structure of these compounds that pair a hydrophobic moiety with a hydrophilic moiety, ethoxylated alcohols such as the present extended branched ethoxylates are a versatile class of compounds commonly referred to as surfactants. Generally, ethoxylate surfactants enhance the mixing and solubilization of oil and water by comprising contrasting moieties within the same compound. Having amphiphilic structure, a single molecule can inhabit the interface of two immiscible phases (i.e. oil and water), effectively bringing them closer together and lowering the interfacial energy ("IFT") associated between them. By lowering this energy, many novel solution applications can be accessed by increasing the homogeneity of these two previously immiscible phases.

Generally, alcohol ethoxylates can vary widely in their properties and applications because the materials used to make these products can vary in their structures and amounts. Conversely, branched alcohols synthesized from petroleum products, including the extended branched alcohols provided herein, offer unique structures in the hydrophobic moiety that are not commonly observed in nature. As further provided, the present extended branched alcohols have specific carbon distributions with lower branching, and can be attained using the EXXAL™ branched alcohols as synthetic starting materials.

Alcohol ethoxylates ("AEOs") are neutral surfactants, widely used in both industrial and consumer product applications. Highly branched AEOs can be characterized as having an inverse relationship between degree of branching and biodegradation. Data developed for AEOs derived from branched $C_8$-rich, $C_9$-rich, $C_{10}$-rich, $C_{13}$-rich and $C_{13}$-rich oxo-alcohols with 1 to 20 moles of ethoxylation is provided in Table 4 immediately below.

TABLE 4

| Alcohol | Alcohol C No. Distribution | Alcohol branches/ molecule | Details Major isomers [Feedstock] | Representative Ethoxylate CAS name/number | EO Range Tested |
| --- | --- | --- | --- | --- | --- |
| EXXAL ™ 8 | 7-9 | 1.59 | methyl-1-heptanols, dimethyl-1-hexanols. [Heptene (proplyene/butene dimer)] | Alcohols, $C_{7-9}$-iso-, $C_8$-rich, ethoxylated 78330-19-5 | 4-10 |
| EXXAL ™ 9 | 8-10 | 1.88 | methyl-1-octanols, dimethyl-1-heptanols. [Octene (Butene-rich olefin dimer)] | Poly(oxy-1,2-ethanediyl), α-isononyl-Ω-hydroxy-(9CI) 56619-62-6; Poly(Oxy-1,2-Ethanediyl), α-Nonyl-Ω-Hydroxy-branched (No CASRN assigned) | 1-20 |
| EXXAL ™ 10 | 9-11 | 2.03 | dimethyl-1-octanols, trimethyl-1-heptanols. [Nonene (propylene trimer)] | Alcohols, $C_{9-11}$-Iso-, $C_{10}$-Rich, Ethoxylated 78330-20-8 | 3-9 |

TABLE 4-continued

| Alcohol | Alcohol C No. Distribution | Alcohol branches/ molecule | Details Major isomers [Feedstock] | Representative Ethoxylate CAS name/number | EO Range Tested |
|---|---|---|---|---|---|
| EXXAL ™ 11 | 10-12 | 2.23 | dimethyl-1-nonanols, trimethyl-1-octanols. [Decenes (Propylene/butene trimer)] | Alcohols, $C_{9-11}$-Branched, Ethoxylated 169107-21-5; Poly(Oxy-1,2-Ethanediyl), α-Isoundecyl-Ω-Hydroxy-(9Ci) 140175-09-3 | 3-10 |
| EXXAL ™ 13 | 12-14 | 3.06 | trimethyl-1-decanols, tetramethyl-1-nonanols. [Dodecenes (Propylene tetramer)] | Alcohols, $C_{11-14}$-iso-, $C_{13}$-rich, ethoxylated 78330-21-9 | 3-12 |

Figure 7:
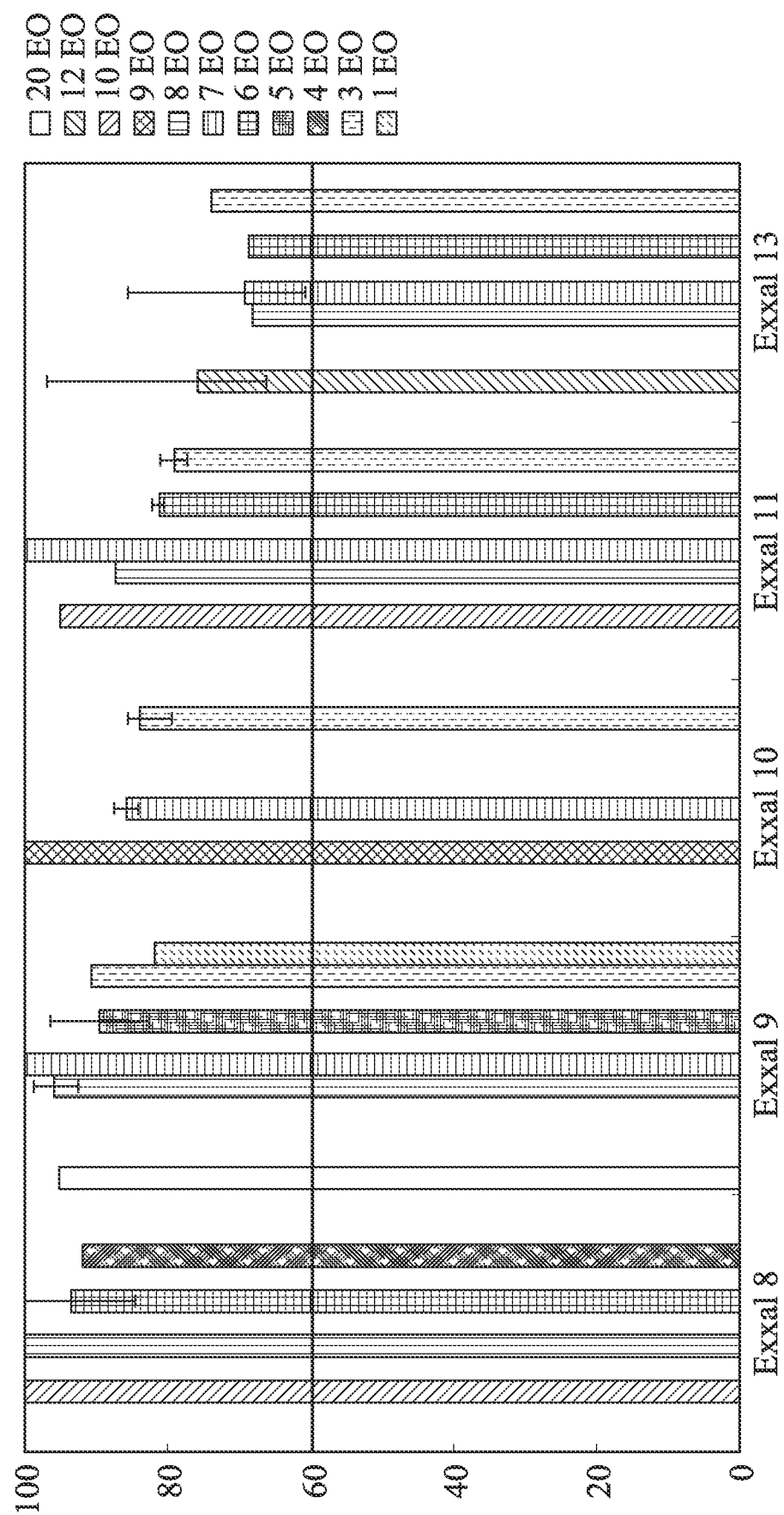
FIG. 7 are bar graphs showing EXXAL™ branched ethoxylates pass the threshold (horizontal line) and classify as readily biodegradable (28 d Manometric Respirometry, Closed Bottle and $CO_2$ Evolution tests). Linear data from Danish EPA (Madsen, 2001), HERA (2009).
Figure 8:
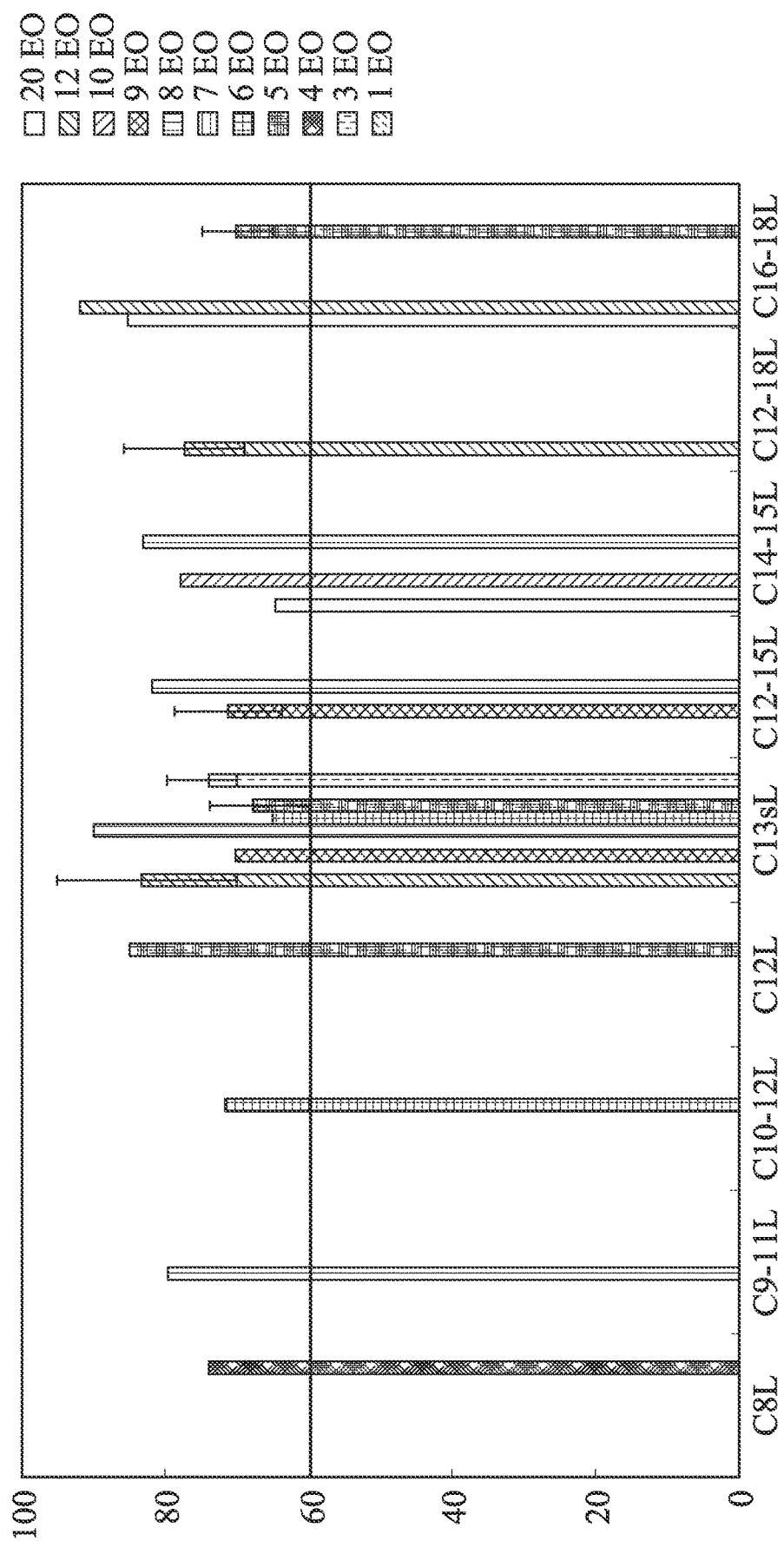
FIG. 8 are bar graphs showing linear alcohol ethoxylates pass the threshold (horizontal line) and classify as readily biodegradable (28 d Manometric Respirometry, Closed Bottle and $CO_2$ Evolution tests). Linear data from Danish EPA (Madsen, 2001), HERA (2009).

Also, as shown in FIG. 7 and FIG. 8, these ethoxylates are readily biodegradable. Biodegradability data for AEOs derived from branched $C_8$-rich, $C_9$-rich, $C_{10}$-rich, $C_{11}$-rich and $C_{13}$-rich oxo-alcohols with 1 to 20 moles of ethoxylate is provided in Table 5 immediately below.

TABLE 5

| Substance | Day 28 % biodeg. | 10d window |
|---|---|---|
| EXXAL ™ 8-4EO | 92 | ✓ |
| EXXAL ™ 8-6EO | 84, 103$^a$ | ✓ |
| EXXAL ™ 8-8EO | 100 | ✓ |
| EXXAL ™ 8-10EO | 107$^a$ | ✓ |
| EXXAL ™ 9-1EO | 82 | ✓ |
| EXXAL ™ 9-3EO | 91 | ✓ |
| EXXAL ™ 9-5EO | 83, 97 | ✓ |
| EXXAL ™ 95-7EO | 102$^a$ | ✓ |
| EXXAL ™ 9-8EO | 93, 99 | ✓ |
| EXXAL ™ 9-20EO | 95 | ✓ |
| EXXAL ™ 10-3EO | 80-86 | ✓* |
| EXXAL ™ 10-7EO | 84, 88 | ✓ |
| EXXAL ™ 10-9EO | 112$^a$ | ✓ |
| EXXAL ™ 11-5EO | 81, 82 | ✓* |
| EXXAL ™ 11-7EO | 106$^a$ | ✓ |
| EXXAL ™ 11-8EO | 87 | ✓ |
| EXXAL ™ 11-10EO | 95 | ✓ |
| EXXAL ™ 13-8EO | 67-68 | ✓* |
| EXXAL ™ 13-12EO | 66-97 | ✓* |

$^a$60% by 7d; 76-95% end of 10-day window.
$^b$Potential inhibition at higher concentrations.
*In some studies AEO surfactants derived from branched $C_8$-rich, $C_9$-rich, $C_{10}$-rich, $C_{11}$-rich and $C_{13}$-rich oxo-alcohols with 1 to 20 moles of ethoxylate meet the OECD readily biodegradable criteria, and are expected to undergo rapid and ultimate degradation in the environment.

As further provided herein, the length of the polyoxyethylene component (i.e. the hydrophilic moiety) of the extended branched ethoxylate provides a class of compounds having unique water solubilities and detergency properties. For example, an increase of ethylene oxide can increase water solubility, as well as increase the hydrophilic/lipophilic balance ("HLB") of the compound. Ranging in arbitrary units of 1-20, the HLB of a nonionic surfactant can be calculated and used to determine the propensity of a compound to work effectively in a given solution of oil and water. Lower HLB values (<10) are commonly used for oil-rich solutions while surfactants with higher HLB values (>10) are typically most efficient in oil-in-water emulsions.

The present extended branched alcohols can be ethoxylated with an alkylene glycol to produce the present extended branched ethoxylates for surfactant applications. Ethoxylation of extended branched alcohols can be prepared by any method suitable for generating ethers, such as Williamson ether synthesis. Ethoxylation methods can include direct reaction of an alcohol with an alkylene glycol or polyalkylene glycol. By way of example, ethoxylation of alcohols with polyols is described in U.S. Pat. No. 3,929,678.

Methods of ethoxylation include activation of an alcohol substituent of an extended branched alcohol by tosylation or substitution of halogenation, followed by reaction with an alkylene glycol or polyalkylene glycol. In an aspect, ethoxylation of an extended branched alcohol 28 can proceed as shown in Scheme IX below. In this example, an extended branched alcohol 28 is reacted with tosyl chloride to generate the corresponding tosylate ester 29, which is then reacted with polyethylene glycol to yield extended branched ethoxylate 30.

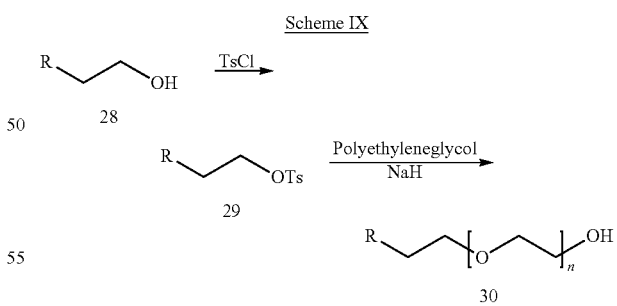

Scheme IX

In addition, ethoxylation is sometimes combined with propoxylation, an analogous reaction using propylene oxide as the monomer. Both reactions are normally performed in the same reactor and can be run simultaneously to give a random polymer, or in alternation to obtain block copolymers such as poloxamers.

Generally, ethoxylates are surfactants useful in products such as laundry detergents, surface cleaners, cosmetics, agricultural products, textiles, and paint. Alcohol ethoxylate-based surfactants are non-ionic and often require longer ethoxylate chains than their sulfonated analogues in order to be water-soluble. Ethoxylation is also practiced, albeit on a much smaller scale, in the biotechnology and pharmaceutical industries to increase water solubility and, in the case of pharmaceuticals, circulatory half-life of non-polar organic compounds. Generally, extended branched ethoxylates are not expected to be mutagenic, carcinogenic, or skin sensitizers, nor cause reproductive or developmental effects. Surfactants The present extended branched alcohols and the extended branched ethoxylates are useful as surfactants or surfactant derivatives. As described herein, surfactants are amphiphilic molecules having two different moieties in a single molecule. Surfactants have a hydrophobic moiety, also referred to as a hydrophobe or tail that can include branched or linear alkyl hydrocarbons, such as branched alcohols, or alkylaryl hydrocarbons, such as nonylphenyl hydrocarbons. Surfactants also have a hydrophilic moiety that can include anionic groups (i.e., sulfates, sulfonates, etc.), nonionic groups (i.e., ethoxylates, propoxylates, etc.), cationic groups (i e amines), or zwitterionic groups (i.e., sultaines, betaines, etc.).

Basically, surfactants act at liquid interfaces to help un-like things go together. For example, surfactants can act at the interface of water and oil to create an emulsion. Surfactants alter the surface and interfacial properties of the liquid. Attaching weak hydrophilic groups to the hydrophobic moiety can reduce solubility and increase the Krafft point. Solubilizers are sometimes added to mitigate solubility problems.

Surface tension or interfacial tension ("IFT") is a surfactant property often reported as force/distance (i.e. N/m) and corresponds to a unit of energy per unit area. The IFT, the free energy required to create more surface interfaces, is reduced when a surfactant is present. Other surfactant properties include cloud point, pour point, foaming, and wetting. Surfactant derivatives based on the present extended branched alcohols are expected to offer improved properties, superior wetting performances, and fewer gel phases.

Surfactants can create stable emulsions for creams and lotions, lift oils and dirt from clothes and skin, help formulation of fluids such as paint, and have numerous other industrial applications such as those as identified in Table 6.

Therefore, surfactants are often used in the production of plasticizers or lubricant esters such as the esters of phthalic acid and anhydride, esters of cyclohexane mono- or dicarboxylic acids, esters of adipic or tri-mellitic acid, esters of the various isomers of pyromellitic acid, and polyol esters. The critical micelle concentrations of the New $C_{13}$ ethoxylate and the New Cis ethoxylate are each in the same range as the commercial product. Therefore, it can be expected that when used in detergents, the New $C_{13}$ ethoxylate and the New $C_{15}$ ethoxylate comprise between about 0.1 wt % and about 1 wt % of a total detergent weight, or between about 0.01 wt % and about 0.1 wt % of a total detergent weight. See, U.S. Pat. No. 4,125,475, col 2. 1. 30-41.

The features of the invention are described in the following non-limiting examples.

Example 1

Preparation of the New $C_{13}$—OH Alcohol and the New $C_{15}$—OH Alcohol

Per Scheme X shown below, the New $C_{13}$—OH alcohol and the New $C_{15}$—OH alcohol were prepared by a two carbon homologation reaction of commercially available branched alcohols, EXXAL™ 11 branched alcohol and EXXAL™ 13 branched alcohol, respectively, to provide the New $C_{13}$ esters and the New $C_{15}$ esters, respectively. The extended branched esters were reduced with lithium aluminum hydride ("LiAlH$_4$") to produce the New $C_{13}$—OH alcohol and the New $C_{15}$—OH alcohol as follows:

Scheme X

EXXAL™ 11 +

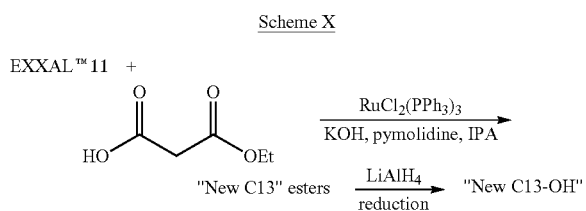

TABLE 6

| Industry | Application | ST/IFT* decrease | Fast wetting | Emulsification | Caustic Stablity | Phase Behavior (less gets) | Low Foaming |
|---|---|---|---|---|---|---|---|
| Textiles | Pretreatment (sizing, scouring, de-sizing) | ✓ | ✓ | ✓ | ✓ | | |
| | Bleaching | | ✓ | | ✓ | | |
| | Dyeing | | ✓ | | | | ✓ |
| Agricultural | Adjuvants (wetting, spreading) | ✓ | | ✓ | | ✓ | ✓ |
| | Suspension concentrates | | ✓ | ✓ | | ✓ | ✓ |
| | Emulsion polymerization | | | ✓ | | ✓ | |
| I&I cleaning | Wetting Agents | | ✓ | | ✓ | ✓ | ✓ |
| | Detergents | | ✓ | ✓ | ✓ | ✓ | ✓ |
| Leather | Wetting, soaking degreasing | | ✓ | ✓ | | ✓ | |
| Petroleum, oil | Enhanced oil recovery | ✓ | | ✓ | | ✓ | |
| | Emulsion breakers | | | | | ✓ | |
| | Dispersants | | | ✓ | | ✓ | |
| Mining | Frothers, flotation | ✓ | | | | ✓ | |
| Detergents | Textiles | ✓ | ✓ | ✓ | | ✓ | |
| | Hard surface cleaners | ✓ | ✓ | | | ✓ | ✓ |
| | Dishwashing - antifoams | | | | | | ✓ |
| Personal Care | Shampoos | | | ✓ | | | |

*ST: surface tension
*IFT: interfacial tension

EXXAL™ 13 +

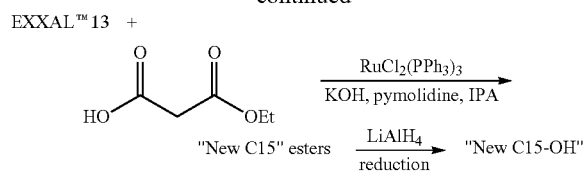

"New C15" esters $\xrightarrow{\text{LiAlH}_4}$ "New C15-OH"
reduction

Specifically, the New $C_{13}$—OH alcohol and the New $C_{15}$—OH alcohol were prepared from EXXAL™ 11 branched alcohol and EXXAL™ 13 branched alcohol, respectively. A multi-neck round-bottom flask was charged with tris(triphenylphosphine) ruthenium (II) dichloride (10 mol %) and potassium hydroxide (0.125 equivalents ("eq.")). A condenser was attached to the flask, and the system was placed under a nitrogen atmosphere. The flask was charged in sequence with toluene (approximately 1 mL per mmol of the EXXAL™ alcohol), pyrrolidine (0.3 eq.), EXXAL™ 11 branched alcohol or EXXAL™ 13 branched alcohol (1 eq.), isopropanol (0.2 eq.), and mono-ethyl malonate (2 eq.). The reaction was then stirred and refluxed for 24 hours under a nitrogen atmosphere. The crude mixture was concentrated under reduced pressure, and resulting material was filtered through FORISOL®, a magnesium silica gel adsorbent useful to separate lipids, with copious amounts of hexane until column eluent was colorless and no more color eluted from the column. This colorless filtrate was then concentrated under reduced pressure and the resulting crude liquid was purified by column chromatography (silica gel) to give a colorless liquid. At this stage, extended branched esters, New $C_{13}$ esters and the New $C_{15}$ esters (each referred to sometimes as an "extended branched ester") were obtained.

by filtration. The filtrate solvent was removed by vacuum to produce the new $C_{15}$—OH alcohol as a clear oil (4.40 g, 99% yield).

Figure 1B:
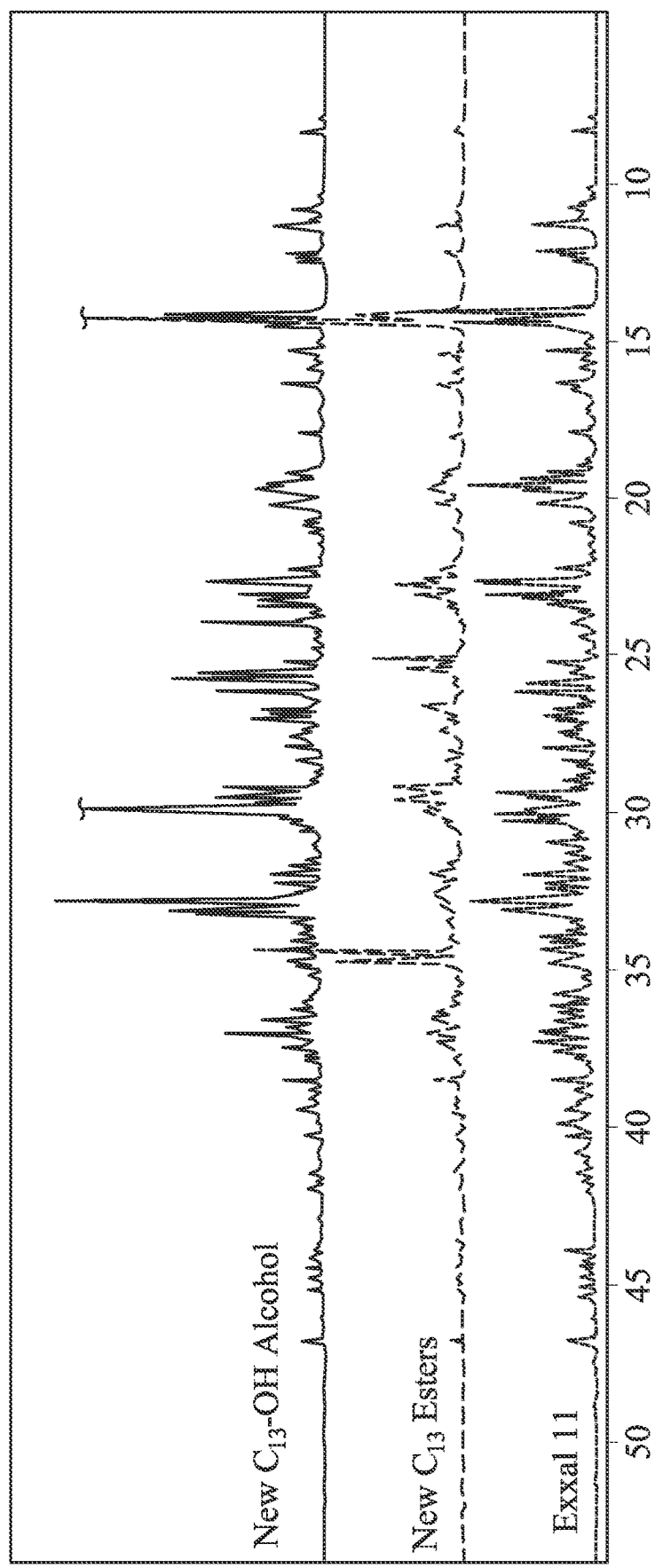
FIG. 1B is the $^{13}C$ NMR spectra of EXXAL™ 11, the New $C_{13}$ esters and the New $C_{13}$—OH alcohol.

A comparison of NMR spectra characterized by $^1$H NMR and $^{13}$C NMR shows that the branching characteristics of the starting material, EXXAL™ 11 branched alcohols, is preserved in the New $C_{13}$ esters as well as in the final product, the New $C_{13}$—OH alcohol. See, FIGS. 1A & 1B.

NMR demonstrated the formation of the extended branched esters and the extended branched alcohols through the reaction path shown immediately above. Based on $^1$H and $^{13}$C NMR, two carbons were added onto the chain of the EXXAL™ 11 branched alcohol, and the structure of branches of the extended branched alcohols, i.e., the New $C_{13}$—OH alcohol, is similar to those of the EXXAL™ 11 branched alcohol.

Figure 2A:
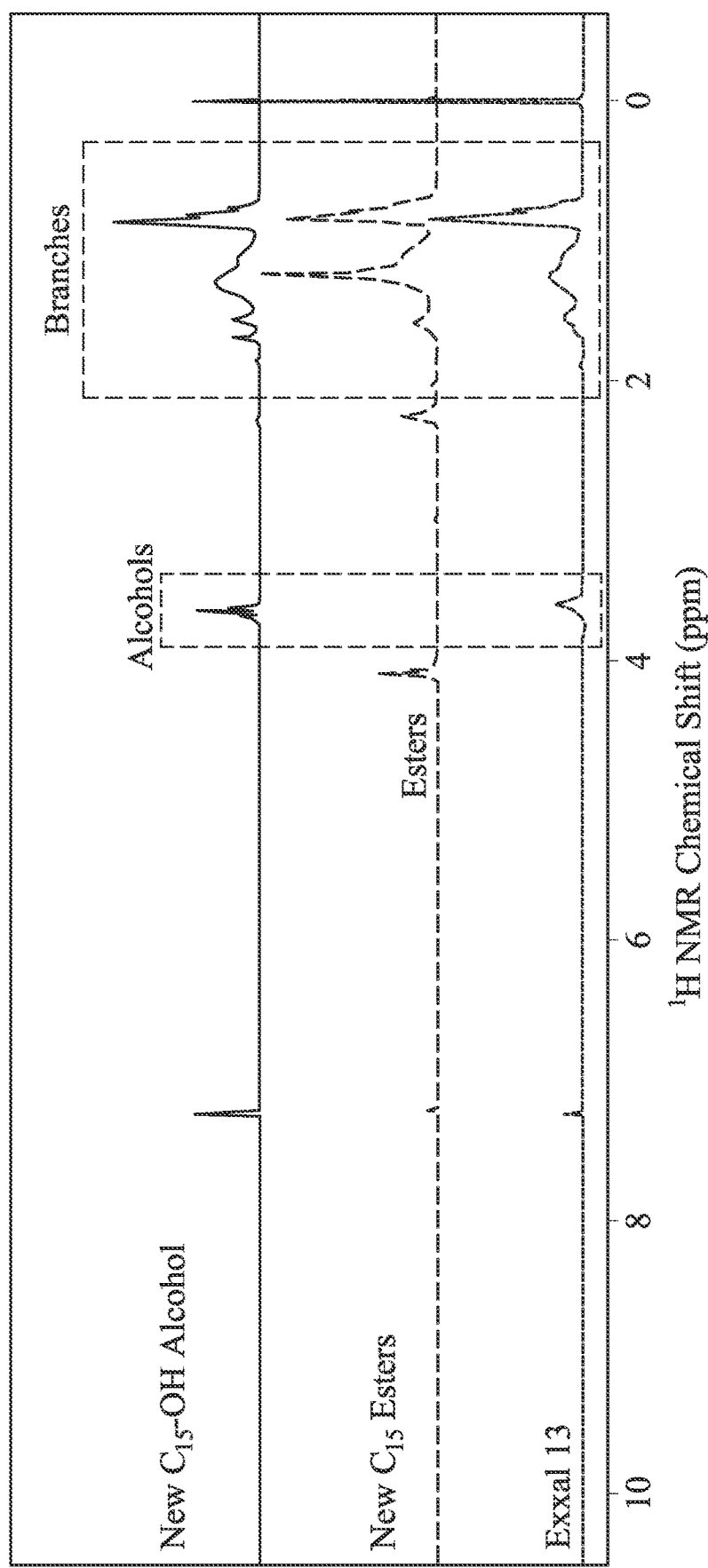
FIG. 2A is the $^1H$ NMR spectra of EXXAL™ 13, the new $C_{15}$ extended branched esters (also referred to herein as the "New $C_{15}$ esters"), and New $C_{15}$ extended branched alcohols (also referred to herein as the "New $C_{15}$—OH alcohol").
Figure 2B:
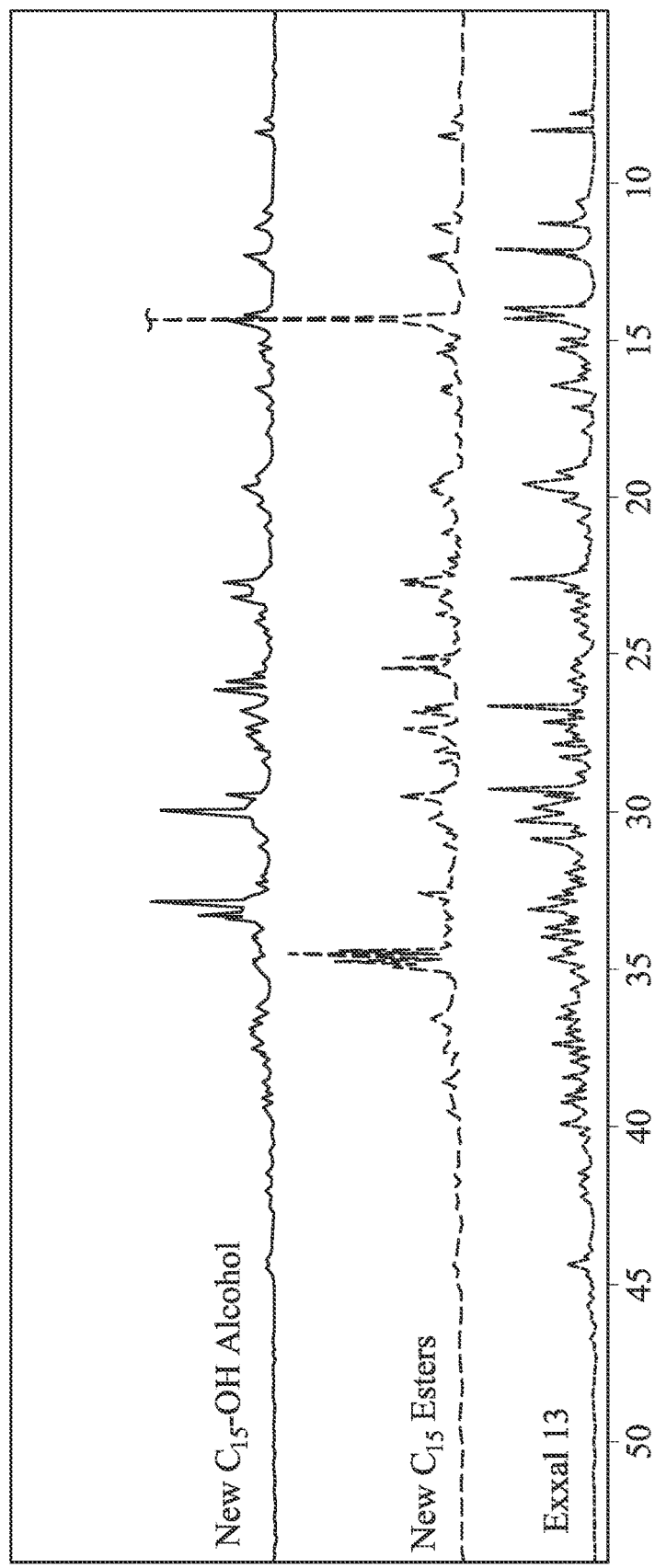
FIG. 2B is the $^{13}C$ NMR spectra of EXXAL™ 13, the New $C_{15}$ esters, and the New $C_{15}$—OH alcohol.

Similarly, FIGS. 2A and 2B shows a similar comparison of NMR spectra for the EXXAL™ 13 branched alcohol conversion into the New $C_{15}$—OH alcohol. The EXXAL™ 13 branched alcohol was preserved in the intermediate structure, New $C_{15}$ esters, as well as in the final product, the New $C_{15}$—OH alcohol. Likewise, NMR demonstrated the formation of new extended branched esters and new extended branched alcohols through the reaction path shown immediately above. Based on $^1$H and $^{13}$C NMR, two carbons were added on the EXXAL™ 13 branched alcohol chain, and the structure of branches of the New $C_{15}$—OH alcohol is similar to those of EXXAL™ 13 branched alcohol.

Table 7 below shows the carbon number distribution of commercial EXXAL™ 11 branched alcohol, EXXAL™ 13 branched alcohol and the New $C_{13}$—OH alcohol. The New $C_{13}$—OH alcohol has a slightly narrower distribution around $C_{13}$ compared to EXXAL™ 13 branched alcohol.

TABLE 7

Structural Comparison of Extended Branched Alcohols with Branched Alcohols

| Compound | Representative Structure | Typical Carbon No. Distribution (GC wt %) | | | | | Average Branching |
|---|---|---|---|---|---|---|---|
| | | $C_{10}$ | $C_{11}$ | $C_{12}$ | $C_{13}$ | $C_{14}$+ | |
| EXXAL™ 11 | | 6.7 | 87.0 | 6.3 | — | — | 2.20 |
| EXXAL™ 13 | | 0.3 | 1.4 | 21.5 | 70.1 | 6.7 | 3.07 |
| New $C_{13}$—OH alcohol | | 0.1 | 5.9 | 12.4 | 78.4 | 3.2 | 1.89 |

New $C_{13}$ esters (6.56 g, 27.11 mmol) were dissolved in tetrahydrofuran ("THF") (170 mL) and LiAlH$_4$ (4.57 g, 4.4 eq) was added. The mixture was heated to reflux for 5 hours and quenched with water dropwise. Magnesium sulfate ("MgSO$_4$") was added and the solids removed by filtration. The filtrate solvent was removed by vacuum to produce the New $C_{13}$—OH alcohol as a clear oil (3.94 g, 73%).

New $C_{15}$ esters (5.10 g, 18.89 mmol) were dissolved in THF (150 mL) and LiAlH$_4$ (2.87 g, 4.0 eq) was added. The mixture was heated to reflux for 5 hours and quenched with water drop wise. MgSO$_4$ was added and the solids removed Carbon number distribution for the extended branched alcohols was measured through GC/MS at EMC-Europe (Machelen). The same characterization method is routinely used for the characterization of the commercial EXXAL™ family Important for household detergent applications is the average branching of the molecules. As demonstrated above, the branching of the starting material (EXXAL™ 11) of 2.2 was preserved or even lowered in the New $C_{13}$—OH alcohol. The branching index is 1.9 and therefore substantially lower than that of commercial EXXAL™ 13 (2.90-3.07).

Since biodegradability is affected by the number of branches, the new product will likely exhibit improved biodegradability rates.

Example 2

Preparation of Extended Branched Ethoxylates

The extended branched alcohols were then converted to new $C_{13}$ tosylates and new $C_{15}$ tosylates through reaction with p-toluenesulfonyl chloride (TsCl). As shown in Scheme XI, the tosylates were then converted to New $C_{13}$ ethoxylate and New $C_{15}$ ethoxylate by reaction with octaethylene glycol in the presence of sodium hydride (NaH).

Scheme XI

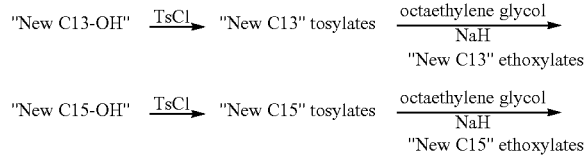

Biodegradability data for the New $C_{13}$ alcohol and the New $C_{15}$ alcohol was obtained according to OECD 301F manometric respirometry test guidelines at test material concentrations of 57 to 100 mg/L. Results are provided in Table 8. Additional biodegradability values are reported in the online database of the European Chemicals Agency (www.echa.europa.eu).

TABLE 8

Biodegradability of Extended Branched Alcohols and Extended Branched Ethoxylates

| Substance | Day 28 % Biodegradability |
| --- | --- |
| EXXAL ™ 11 | 71 |
| EXXAL ™ 13 | 61 |
| New $C_{13}$-OH alcohol | 72 |
| New $C_{15}$-OH alcohol | 67 |
| EXXAL ™ 11-3EO | 77, 81 |
| EXXAL ™ 11-5EO | 81, 82 |
| EXXAL ™ 11-7EO | 106 |
| EXXAL ™ 11-8EO | 87 |
| EXXAL ™ 11-10EO | 95 |
| EXXAL ™ 13-7EO | 61-86 |
| EXXAL ™ 13-8EO | 67-68 |
| EXXAL ™ 13-12EO | 66-97 |

Figure 3:
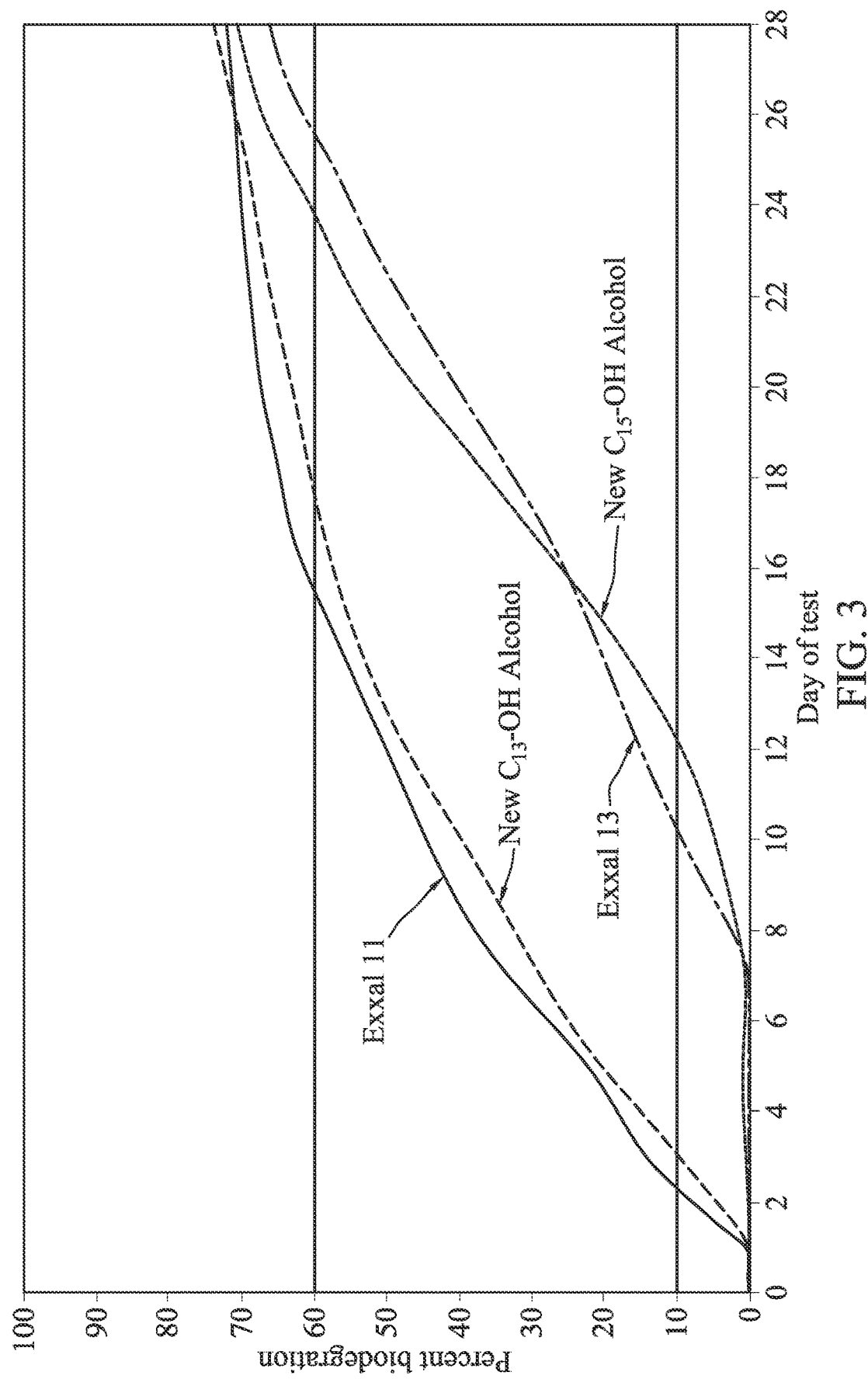
FIG. 3 depicts biodegradation over time for each of the EXXAL™ 11 branched alcohols, EXXAL™ 13 branched alcohols, the New $C_{13}$—OH alcohol, and the New $C_{15}$—OH alcohol.

FIG. 3 is a graphical representation showing biodegradability data according to OECD 301F manometric respirometry test for EXXAL™ 11, EXXAL™ 13, New $C_{13}$—OH alcohol, and New $C_{15}$—OH alcohol. All samples assayed achieved a minimum of at least 60% biodegradation within 28 days.

Figure 4:
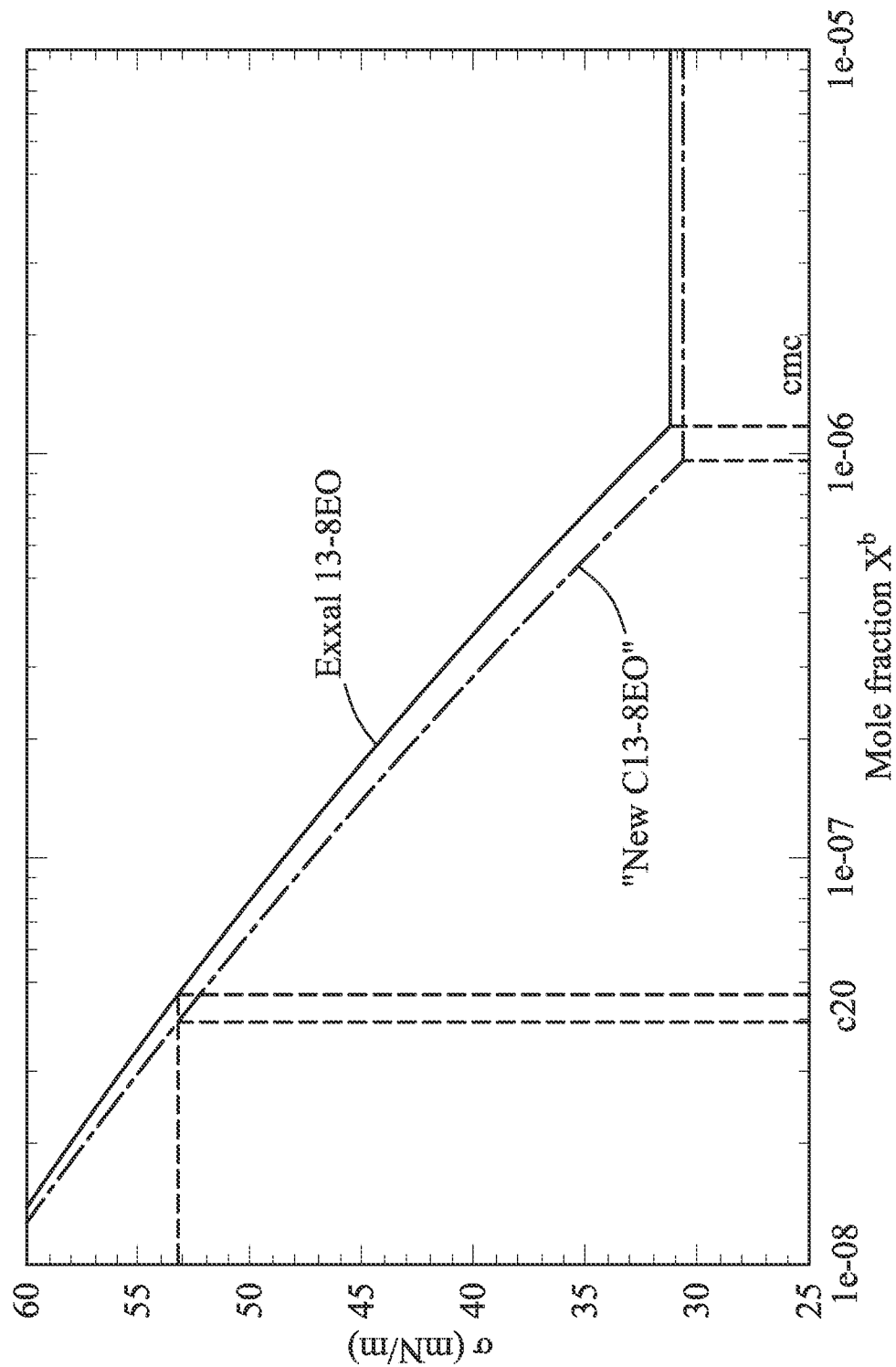
FIG. 4 is a calculated surface tension isotherm of EXXAL™ 13 branched ethoxylate and new $C_{13}$ extended branched ethoxylates (also referred to herein as "New $C_{13}$ ethoxylate").

Next, we compared interfacial property performance. Improved biodegradability of the new product should not be achieved at the expense of other important performance attributes, such as surface tension reduction, critical micelle concentration and the efficiency c20. All these attributes can be obtained from a surface tension isotherm. Using a method developed by V. Sresht, E. P. Lewandowski, D. Blankschtein, A. Jusufi, *Langmuir* 33, 8319 (2017) in which Molecular Dynamics (MD) simulations were combined with Molecular-Thermodynamic Theory (MTT), we calculated surface tension isotherms of ethoxylated EXXAL™ 13 branched alcohol and the New $C_{13}$ ethoxylate, as shown in FIG. 4 where "New $C_{13}$-8EO" refers to the New $C_{13}$ ethoxylate and where '8EO' indicates octaethylene glycol functionalization.

In addition, Table 9 provides surface tension data for the EXXAL™ 13 ethoxylate and the New $C_{13}$ ethoxylate.

TABLE 9

Surface Tension Isotherm at 22° C.

| Molarity [mol/L] | EXXAL ™ 13-8EO |
| --- | --- |
| 0 | 72.3 |
| 1.54334E-08 | 73.8 |
| 4.19523E-08 | 72.1 |
| 1.14038E-07 | 69.8 |
| 3.09988E-07 | 64.2 |
| 8.42635E-07 | 59.8 |
| 2.29052E-06 | 54.1 |
| 6.22628E-06 | 31.9 |
| 1.69248E-05 | 30 |
| 4.60064E-05 | 28.9 |
| 0.000125058 | 27.8 |
| 0.000339945 | 27.7 |

| Molarity [mol/L] | New $C_{13}$-8(EO) |
| --- | --- |
| 0 | 71.8 |
| 8.42635E-07 | 58 |
| 2.29052E-06 | 52.5 |
| 6.22628E-06 | 46.3 |
| 1.69248E-05 | 38.5 |
| 4.60064E-05 | 31.3 |
| 0.000125058 | 31.2 |
| 0.000339945 | 31.7 |
| 0.000924077 | 31.5 |

The EXXAL™ 13-8EO and the New $C_{13}$ ethoxylate mixtures include branched ethoxylates of the structural formula of:

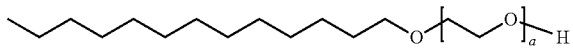

having the formula of $C_{29}H_{60}O_9$, an average molecular weight of 552.79 g/mol as well as branched isomer and +/−C atoms.

Figure 6:
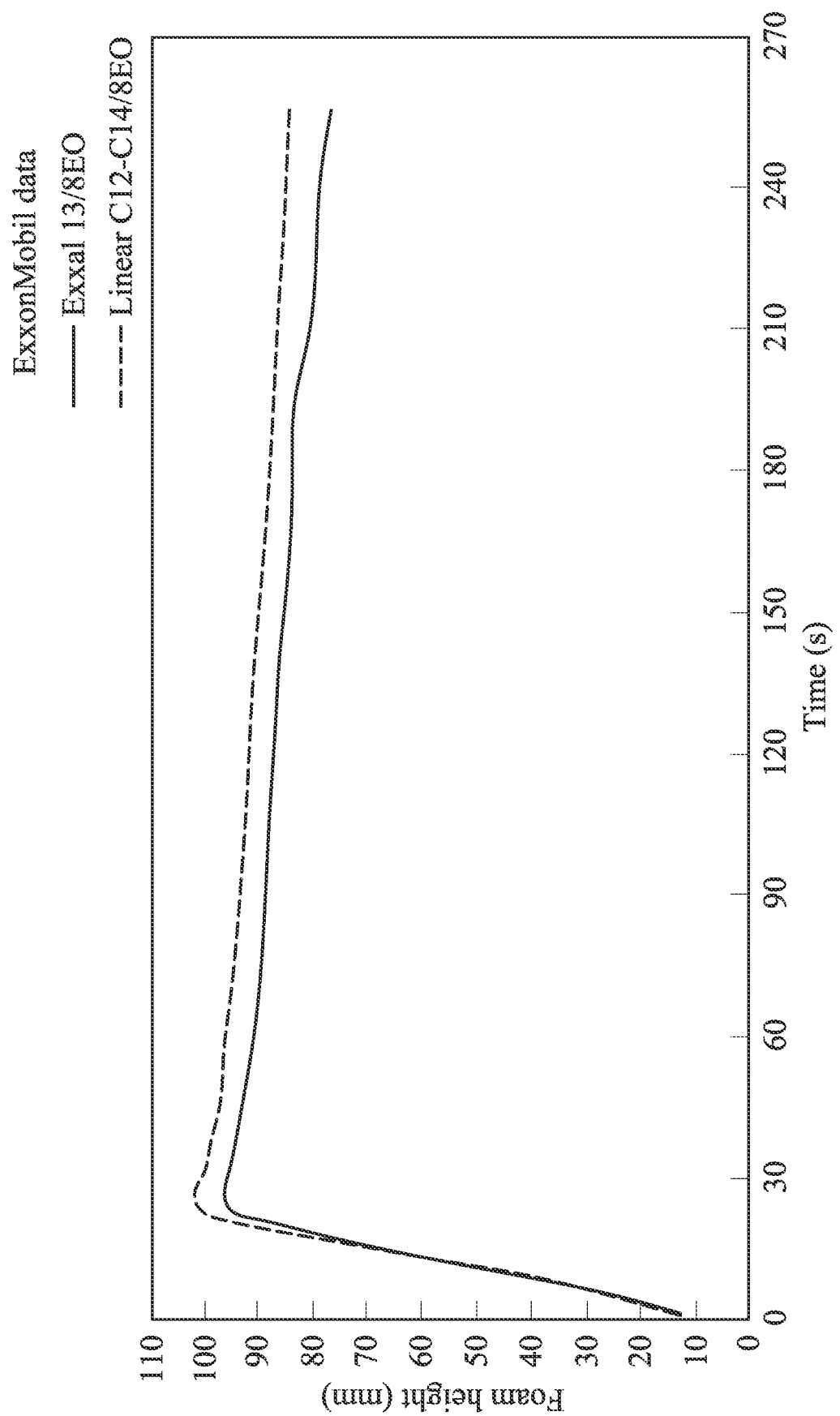
FIG. 6 is a graph depicting foam height over time for EXXAL™ 13 branched ethoxylate and a linear $C_2$-$C_4$ ethoxylate.

Based on comparisons of these two compounds, it was found that due to a slightly narrower distribution around $C_{13}$ species the efficiency is slightly improved. From the surface tension isotherm calculations shown in FIG. 4, we found that the CMC of the new product is about 20% lower, and the c20 is around 15% lower when the New $C_{13}$ ethoxylate is compared to the commercial Exxal 13-8EO. The surface tension reduction at the CMC is statistically identical. In summary, our data suggests that the lower branching of the New $C_{13}$ ethoxylate performs better in terms of biodegradability and surface tension efficiency compared to the commercial EXXAL™ 13 branched alcohol-based surfactants, provided that the hydrophilic parts (the ethoxylated groups) are identical. It is anticipated that foaming properties are similar to those provided in FIG. 6.

Figure 5:
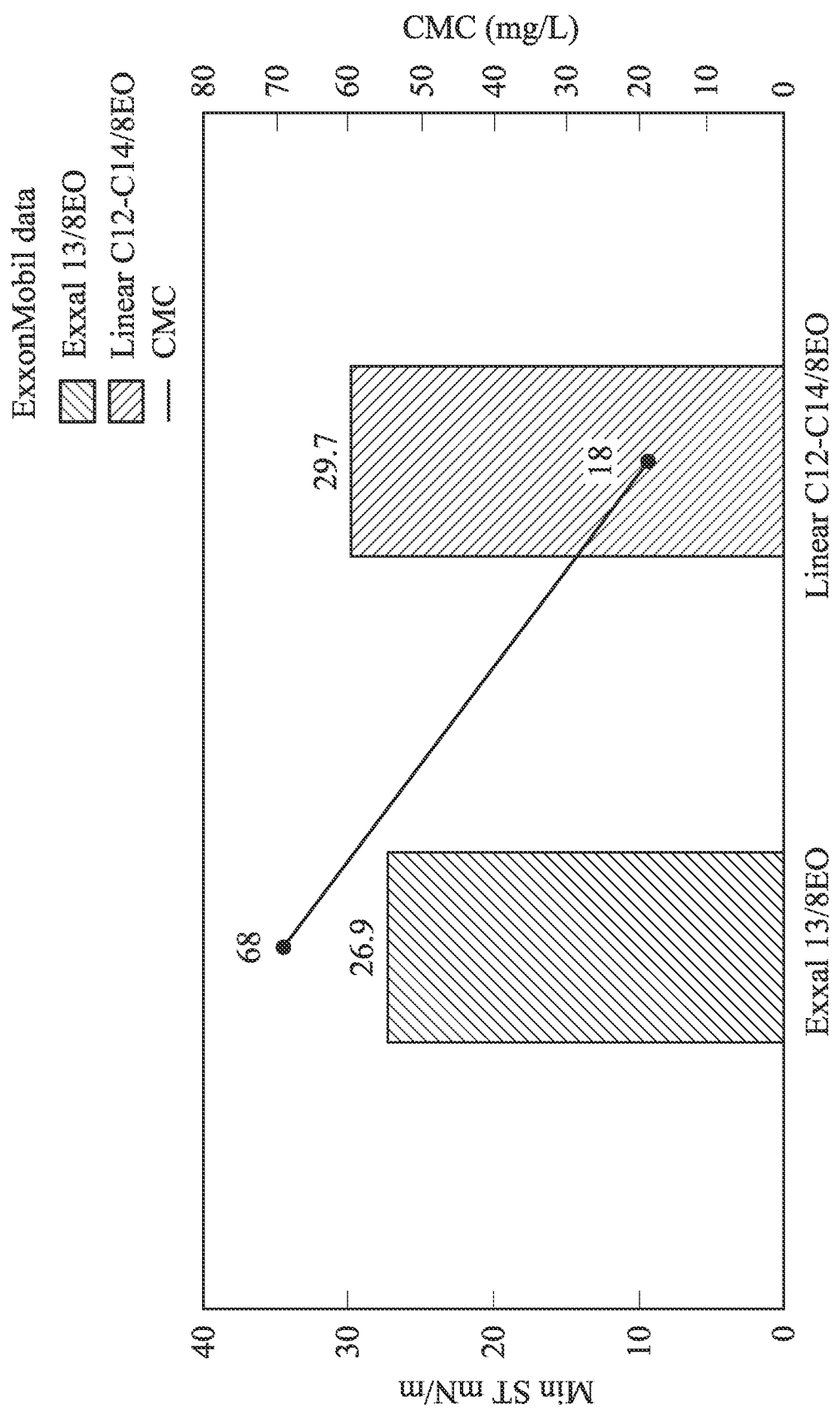
FIG. 5 shows surface tensions at the critical micelle concentration for EXXAL™ 13 branched ethoxylate and a linear $C_{12}$-$C_{14}$ ethoxylate.

In comparison, FIG. 5 provides surface tensions for EXXAL™ 13 branched ethoxylate and linear $C_{12}$-$C_{14}$ ethoxylate.

We claim:

1. A compound having a structural formula selected from the group consisting of:

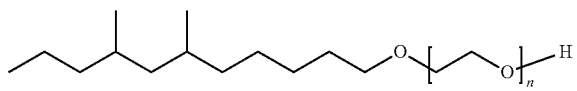

wherein n is an integer from 1 to 12; and

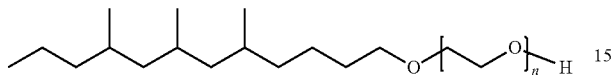

wherein n is an integer from 1 to 12.

2. A mixture comprising a plurality of compounds, having a structural formula selected from the group consisting of:

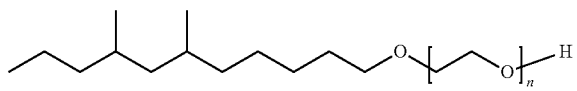

wherein n is an integer from 1 to 12; and

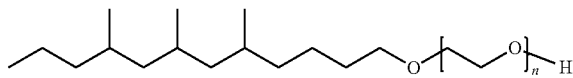

wherein n is an integer from 1 to 12.

3. The mixture of claim 2, wherein the mixture further comprises isomers of one or more of the plurality of compounds.

4. The mixture of claim 2, wherein the mixture has a carbon distribution number between about 10 and about 14.

5. A surfactant comprising a compound of the structural formula of claim 1.

6. A surfactant comprising a plurality of compounds of the structural formula of claim 1.

7. The compounds of claim 1, wherein the compound is readily biodegradable in accordance with OECD 301 F.

8. The compounds of claim 1, wherein the compound reduces surface tension between about 15 percent and about 20 percent when compared to the ethoxylated form of other branched alcohols.

9. A method of making a mixture of extended branched alcohols comprising the steps of
providing a branched alcohol;
reacting the branched alcohol with a half-ester to provide an extended branched ester; and
reducing the extended branched ester to provide an extended branched alcohol,
wherein the mixture of extended branched alcohols comprises a plurality of compounds having a formula selected from the group consisting of:

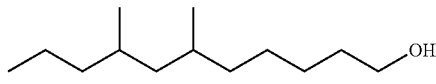

wherein the amount of the plurality of compounds is at least 70 wt. %; and

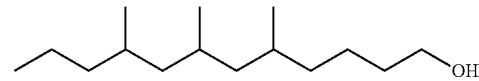 [SMILES: CCCC(C)CC(C)CC(C)CCCCO]

wherein the amount of the plurality of compounds is at least 70 wt. %.

10. The method of claim 9, wherein the half-ester is monoethyl malonate.

11. The method of claim 9, wherein the extended branched ester is reduced by dissolving the extended branched ester in tetrahydrofuran.

12. A method of making a mixture of extended branched alcohols comprising the steps of
forming an aldehyde from a branched alcohol;
converting the aldehyde to form an extended branched ester; and
reducing the extended branched ester to produce an extended branched alcohol,
wherein the mixture of extended branched alcohols comprises a plurality of compounds having a formula selected from the group consisting of:

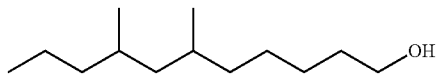

wherein the amount of the plurality of compounds is at least 70 wt. %; and

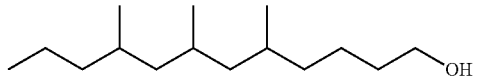 [SMILES: CCCC(C)CC(C)CC(C)CCCCO]

wherein the amount of the plurality of compounds is at least 70 wt. %.

13. The method of claim 12, wherein an aldehyde is formed by hydrogen abstraction.

14. The method of claim 12, wherein the aldehyde is condensed with a reagent to form the extended branched ester.

* * * * *